United States Patent
Trabanco-Suárez et al.

(10) Patent No.: US 10,106,524 B2
(45) Date of Patent: Oct. 23, 2018

(54) 2,3,4,5-TETRAHYDROPYRIDIN-6-AMINE AND 3,4-DIHYDRO-2H-PYRROL-5-AMINE COMPOUND INHIBITORS OF BETA-SECRETASE

(71) Applicant: Janssen Pharmaceutica NV, Beerse (BE)

(72) Inventors: Andrés Avelino Trabanco-Suárez, Olias del Rey (ES); Óscar Delgado-González, Madrid (ES); Henricus Jacobus Maria Gijsen, Breda (NL); Michiel Luc Maria Van Gool, Madrid (ES); Sven Franciscus Anna Van Brandt, Beerse (BE); Michel Anna Jozef De Cleyn, Lille (BE); Santos Fustero Lardiés, Valencia (ES); Natalia Mateu Sanchís, Cambridge (GB)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/536,474

(22) PCT Filed: Dec. 16, 2015

(86) PCT No.: PCT/EP2015/079981
§ 371 (c)(1),
(2) Date: Jun. 15, 2017

(87) PCT Pub. No.: WO2016/096979
PCT Pub. Date: Jun. 23, 2016

(65) Prior Publication Data
US 2017/0362198 A1    Dec. 21, 2017

(30) Foreign Application Priority Data

Apr. 22, 2015  (EP) .................... 15164704

(51) Int. Cl.
| | | |
|---|---|---|
| *A61K 31/4965* | (2006.01) | |
| *C07D 401/12* | (2006.01) | |
| *C07D 401/10* | (2006.01) | |
| *A61K 31/444* | (2006.01) | |
| *A61K 31/497* | (2006.01) | |
| *A61K 31/506* | (2006.01) | |

(52) U.S. Cl.
CPC .......... *C07D 401/12* (2013.01); *A61K 31/444* (2013.01); *A61K 31/497* (2013.01); *A61K 31/506* (2013.01); *C07D 401/10* (2013.01)

(58) Field of Classification Search
CPC .. A61K 31/497; A61K 31/506; A61K 31/444; C07D 401/10; C07D 401/12
USPC ........... 514/256, 255.05, 336; 544/335, 408; 546/268.1
See application file for complete search history.

(56) References Cited

U.S. PATENT DOCUMENTS

| | | | |
|---|---|---|---|
| 4,188,389 | A | 2/1980 | Jirkovsky |
| 5,292,732 | A | 3/1994 | Rover |
| 8,207,164 | B2 | 6/2012 | Holzer |
| 8,846,658 | B2 | 9/2014 | Veenstra |
| 2005/0282825 | A1 | 12/2005 | Malamas |
| 2007/0005404 | A1 | 1/2007 | Raz |
| 2007/0225372 | A1 | 9/2007 | Bueno Melendo |
| 2008/0051420 | A1 | 2/2008 | Berg |
| 2009/0082560 | A1 | 3/2009 | Kobayashi |
| 2011/0009395 | A1 | 1/2011 | Audui et al. |

(Continued)

FOREIGN PATENT DOCUMENTS

| | | |
|---|---|---|
| CA | 2825620 | 9/2012 |
| EP | 2147914 | 1/2010 |

(Continued)

OTHER PUBLICATIONS

Cheret et al. 2013 EMBO Journal, "Bace1 and Neuregulin-1 cooperate to control formation and maintenance of muscle spindles", (2013), 32(14), 2015-2028.

(Continued)

*Primary Examiner* — Jeffrey H Murray
(74) *Attorney, Agent, or Firm* — Yuriy P. Stercho

(57) ABSTRACT

The present invention relates to 2,3,4,5-tetrahydropyridin-6-amine and 3,4-dihydro-2H-pyrrol-5-amine compound inhibitors of beta-secretase having the structure shown in Formula (I)

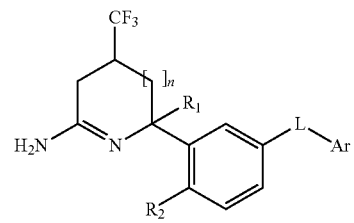

wherein the radicals are as defined in the specification. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease, dementia associated with beta-amyloid, age-related macular degeneration, type 2 diabetes or metabolic disorders.

16 Claims, No Drawings

(56) References Cited

U.S. PATENT DOCUMENTS

| | | |
|---|---|---|
| 2012/0238557 A1 | 9/2012 | Masui et al. |
| 2012/0277244 A1 | 11/2012 | Tintelnot-Blomley |
| 2014/0128385 A1 | 5/2014 | Rueeger |
| 2014/0256715 A1 | 9/2014 | Hurth et al. |
| 2016/0152581 A1 | 6/2016 | Trabanco-Suarez et al. |

FOREIGN PATENT DOCUMENTS

| | | |
|---|---|---|
| EP | 2518 059 | 10/2012 |
| JP | 2012-512831 | 6/2012 |
| JP | 2013-513563 | 4/2013 |
| JP | 2012-147763 | 7/2014 |
| JP | 2014-505688 | 3/2015 |
| WO | WO 1998/057641 | 12/1998 |
| WO | WO 2003/089434 | 10/2003 |
| WO | WO 2004/026877 | 4/2004 |
| WO | WO 2004/058176 | 7/2004 |
| WO | WO 2005/037832 | 4/2005 |
| WO | WO 2006/034093 | 3/2006 |
| WO | WO 2006/076284 | 7/2006 |
| WO | WO 2006/138265 | 12/2006 |
| WO | WO 2007/058583 | 5/2007 |
| WO | WO 2007/114771 | 10/2007 |
| WO | WO 2007/005404 | 11/2007 |
| WO | WO 2009/022961 | 2/2009 |
| WO | WO 2009/058300 | 5/2009 |
| WO | WO 2009/097278 | 8/2009 |
| WO | WO 2009/102468 | 8/2009 |
| WO | WO 2009/134617 | 11/2009 |
| WO | WO 2010/070008 | 6/2010 |
| WO | WO 2011/002409 | 1/2011 |
| WO | WO 2011/009943 | 1/2011 |
| WO | WO 2011/020806 | 2/2011 |
| WO | WO 2011/069934 | 6/2011 |
| WO | WO 2011/071135 | 6/2011 |
| WO | WO 2011/080176 | 7/2011 |
| WO | WO 2011/154374 | 12/2011 |
| WO | WO 2011/154431 | 12/2011 |
| WO | WO 2012/000933 | 1/2012 |
| WO | WO 2012/038438 | 3/2012 |
| WO | WO 2012/057247 | 5/2012 |
| WO | WO 2012/085038 | 6/2012 |
| WO | WO 2012/095463 | 7/2012 |
| WO | WO 2012/098064 | 7/2012 |
| WO | WO 2012/117027 | 9/2012 |
| WO | WO 2012/120023 | 9/2012 |
| WO | WO 2012/147763 | 11/2012 |
| WO | WO 2013/083556 | 6/2013 |
| WO | WO 2013/083557 | 6/2013 |
| WO | WO 2014/099794 | 6/2014 |
| WO | WO 2014/198851 | 12/2014 |
| WO | WO 2014/198853 | 12/2014 |
| WO | WO 2014/198854 | 12/2014 |
| WO | WO 2016/096979 | 6/2016 |

OTHER PUBLICATIONS

Esterhazy et al_Cell Metabolism, "Bace2 is a β Cell-Enriched Protease that Regulates Pancreatic β Cell Function and Mass",_ 2011_14_365-377.

Fleck et al. 2012, Curr. Alzheimer Res., "Bace1Dependent Neuregulin Processing: review" 9, 178-183.

Ginman, et al., "Core refinement toward Permeable β-Secretase (BACE-1) Inhibitors with Low HERG Activity", Journal of Medicinal Chemistry, vol. 56, pp. 4181-4205, 2013.

Hackam, et al. JAMA, "Translation of Research Evidence From animals to Humans", 296(14), 2006, 1731-1732.

Haniu et al., 2000, J. Biol. Chem., "Protein Structure and folding: Characterization of Alzheimer's β-secretase protein BACE: a Pepsin Family member with Unusual Properties", 275, 21099-21106.

Hemming et al. 2009, PLoS ONE, "Identification of β-Secretase (BACE1) Substrates using Quantitative Proteomics", 4, e8477.

Hilpert, et al., "β-Secretase (BACE1) Inhibitors with High in vivo efficacy Suitable for Clinical Evaluation in Alzheimer's Disease", Journal of Medicinal Chemistry, vol. 56, No. 10, pp. 3980-3995, 2013.

Hong et al, 2000, Science, "Structure of the Protease domain of memapsin 2(β-Secretase) Complexed with Inhibitor" 290, 150-153.

J. G. Cannon, Chapter Nineteen in Burger's Medicinal Chemistry and Drug Discovery, Fifth edition, vol. I: Principles and Practice, Wiley-Interscience 1995, pp. 783-802, 784.

Jonsson et al. 2012, Nature, "A mutation in APP protects against Alzheimer's disease and age-related cognitive decline", 488, 96-99.

Jordan, V. C. Nature Reviews: Drug Discovery,"Tamoxifen: A Most Unlikely Pioneering Medicine", 2, 2003, 205.

Kim et al. 2011, J. Biol. Chem. "Molecular Bases of Disease: Reduced Sodium Channel Nav1.1 Levels in BACE1-null Mice", 286, 8106-8116.

Koike H et al.,J Biochem., "Thimet Oligopeptidase Cleaves the Full-Length Alzheimer Amyloid Precursor Protein at a β-Secretase Cleavage Site in COS Cells" 1999, 126, 235-42.

Kondoh et al. Breast Cancer Res.Treat., "A novel aspartic protease gene, ALP56, is up-regulated in human breast cancer independently from the cathepsin D gene", 2003, vol. 78, pp. 37-44.

Kuhn et al. 2012, EMBO J. "Secretome protein enrichment identifies physiological BACE1protease substrates in neurons" 31, 3157-3168.

Kuhn et al. J. Biol. Chem."Protein Synthesis, Post-translation Modification, and Degradation: Regulated Intramembrane Proteolysis of the Interleukin-1 receptor II by α-,β-, and γ-Secretase", 2007, vol. 282, No. 16, pp. 11982-11995.

Luo et al., 2001, Nat. Neurosci, "Mice deficient in BACE!, the Alzheimer's β-secretase, have normal phenotype and abolished β-amyloid generation", 4, 231-232.

Martic-Kehl et al., Eur J. Nucl Med Mol Imaging (2012) 39:1492-1496.

Mateu et al., Chem. Eur. J. 2015, 21, 11719-11726.

Naus et al. 2004, J. Biol. Chem.,"Enzyme Catalysis and Regulation: Extodomain Shedding of the Neural Recognition Molecule CHL1 by the Metalloprotease-disintegrin ADAM8 Promotes Neurite Outgrowth and Suppresses Neuronal Cell Death", 279, 16083-16090.

Oehlrich et al, The evolution of amidine-based brain penetrant BACE1 inhibitors_Bioorganic & Medicinal Chemistry Letters, 2014, vol. 24, pp. 2033-2045.

Ostermann et al, 2006, Journal of molecular biology, "Crystal Structure of Human BACE2 in Complex with a Hydroxyethylamine transition-state Inhibitor", 355, (2), 249-61.

Park, et al., Effects of Flourine Substitution on Drug Metabolism: Pharmacological and Toxicological Impficatins*, Drug metabolism reviews, vol. 26(3), 1994, pp. 605-643.

Park, et al., "Metabolism of Fluorine-Containing Drugs", Annual Ref. Pharmacol. Toxicol. 2001, vol. 41, pp. 443-470.

Patani et al, Chem.Rev., "Bioisosterism: A Rational Approach in Drug Design", 1996, 96, 3147-3176.

Purser, et al., "Flourine in Medicinal Chemistry", Chemical Society Reviews, 2008, vol. 37, pp. 320-330.

Roberds et al., 2001, Hum. Mol. Genet, "BACE knockout mice are healthy despite lacking the primary β-secretase activity in the brain: implications for Alzheimer's disease therapeutics",10, 1317-1324.

Rochin et al. PNAS, "BACE2 processes PMEL to form the melanosome amyloid matrix in pigment cells", Jun. 25, 2013, vol. 110, No. 26, pp. 10658-10663.

Sheridan, et al., "The Most Common Chemical Replacements in Drug-Like Compounds", J. Chem. Inf. Comput. Sci., 2002 vol. 42, pp. 103-108.

Silvestri_Medicinal Research Reviews, "Boom in the development of Non-Peptidic β-secretase (BACE1) Inhibitors for the Treatment of Alzheimer's Disease", 295-238_2009.

Stutzer et al. 2013, J. Biol. Chem., "Systematic Proteomic Analysis Identifies β-Site Amyloid Precursor Protein Cleaving Enzyme 2 and 1 (BACE2 and BACE1) Substrates in Pancreatic β-Cells" 288, 10536-10547.

Vassar et al., J. Neurochem., "Function, therapeutic potential and cell biology of BACE proteases: current status and future prospects", (2014) 10.1111/jnc.12715.

(56) References Cited

OTHER PUBLICATIONS

Vippagunta, et al. Advanced Drug Delivery Reviews, "Crystalline Solids", 48, 2001, 18.
Wang et al. Trends in Pharmacological Sciences, Apr, "β-Secretase: its biology as a therapeutic target in diseases", 2013, vol. 34, No. 4, pp. 215-225.
Wang, et al., Fluroine in Pharmaceutical Industry: Flourine-Containing Drugs Introduced to the Market in the Last Decade (2001-2011), Chemical Review, pp. 2432-2506, 2014.
Willem et al. 2009, Semin. Cell Dev. Biol., Function, regulation and therapeutic properties of β-secretase (BACE1) 20, 175-182.
Woltering, et al., "BACE Inhibitors: A head group scan on a series of amides:", Biorganic & Medicinal Chemistry Letters, vol. 23, pp. 4239-4243, 2013.
Yan and Vassar Lancet Neurol. "Targeting the β secretase BACE1 for Alzheimer's disease therapy", 2014, vol. 13, pp. 319-329.
Yan et al. J Alzheimers Dis. "Can BACE! Inhibition Mitigate Early Axonal Pathology in Neurological Diseases?", 2014, 30 vol. 38, No. 4, pp. 705-718.
Zhang, et al, "Application of Amybidbeta Protein in the Diagnosis of Alzheimer's Disease", vol. 29, No. 1, 2008 (see English translation as provided).
Zhou et al. 2012, J. Biol. Chem. "The Neural Cell Adhesion Molecules L1 and CHL1 are Cleaved by BACE1 Protease in Vivo", 287, 25927-25940.
Decision from the European Patent Office dated Mar. 3, 2017 revoking the European Patent No. 2456763.
International Search Report and Written Opinion—PCT/EP2011/059441.
International Search Report and Written Opinion—PCT/EP2011/059330.
International Search Report and Written Opinion—PCTEP2011/060712.
International Search Report and Written Opinion—PCT/EP2011/066343.
International Search Report and Written Opinion—PCT/EP2011/073522.
International Search Report and Written Opinion—PCT/EP2012/053455.
International Search Report and Written Opinion—PCT/EP2012/053863.
International Search Report and Written Opinion—PCT/EP2012/074349.
International Search Report and Written Opinion—PCT/EP2012/074351.
International Search Report and Written Opinion—PCT/EP2015/079981.
International Search Report and Written Opinion—PCT/EP2014/062285.
International Search Report and Written Opinion—PCT/EP2014/062286.
International Search Report and Written Opinion—PCT/EP2014/062283.

2,3,4,5-TETRAHYDROPYRIDIN-6-AMINE AND 3,4-DIHYDRO-2H-PYRROL-5-AMINE COMPOUND INHIBITORS OF BETA-SECRETASE

CROSS REFERENCE TO RELATED APPLICATIONS

This application is the national stage of PCT Application No. PCT/EP2015/079981, filed Dec. 16, 2015, which claims priority from European Patent Application No. 14198977.2, filed Dec. 18, 2014 and European Patent Application No. 15164704.7, filed Apr. 22, 2015, the entire disclosures of which are hereby incorporated in their entirety.

FIELD OF THE INVENTION

The present invention relates to 2,3,4,5-tetrahydropyridin-6-amine and 3,4-dihydro-2H-pyrrol-5-amine compound inhibitors of beta-secretase having the structure shown in Formula (I)

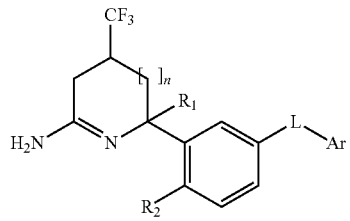

wherein the radicals are as defined in the specification. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease, dementia associated with beta-amyloid, age-related macular degeneration, type 2 diabetes and other metabolic disorders.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about one in ten people at age 65 have AD while at age 85, one out of every two individuals are afflicted by AD. The average life expectancy from the initial diagnosis is 7-10 years, and AD patients require extensive care either in an assisted living facility or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of beta-amyloid 1-42 (Abeta 1-42) peptide. Abeta 1-42 forms oligomers and then fibrils, and ultimately amyloid plaques. The oligomers and fibrils are believed to be especially neurotoxic and may cause most of the neurological damage associated with AD. Agents that prevent the formation of Abeta 1-42 have the potential to be disease-modifying agents for the treatment of AD. Abeta 1-42 is generated from the amyloid precursor protein (APP), comprised of 770 amino acids. The N-terminus of Abeta 1-42 is cleaved by beta-secretase (BACE1), and then gamma-secretase cleaves the C-terminal end. In addition to Abeta 1-42, gamma-secretase also liberates Abeta 1-40 which is the predominant cleavage product as well as Abeta 1-38 and Abeta 1-43. These Abeta forms can also aggregate to form oligomers and fibrils. Thus, inhibitors of BACE1 would be expected to prevent the formation of Abeta 1-42 as well as Abeta 1-40, Abeta 1-38 and Abeta 1-43 and would be potential therapeutic agents in the treatment of AD.

Type 2 diabetes (T2D) is caused by insulin resistance and inadequate insulin secretion from pancreatic beta-cells leading to poor blood-glucose control and hyperglycemia. Patients with T2D have an increased risk of microvascular and macrovascular disease and a range of related complications including diabetic nephropathy, retinopathy and cardiovascular disease. The rise in prevalence of T2D is associated with an increasingly sedentary lifestyle and high-energy food intake of the world's population.

Beta-cell failure and consequent dramatic decline in insulin secretion and hyperglycemia marks the onset of T2D. Most current treatments do not prevent the loss of beta-cell mass characterizing overt T2D. However, recent developments with GLP-1 analogues, gastrin and other agents show that preservation and proliferation of beta-cells is possible to achieve, leading to an improved glucose tolerance and slower progression to overt T2D.

Tmem27 has been identified as a protein promoting beta-cell proliferation and insulin secretion. Tmem27 is a 42 kDa membrane glycoprotein which is constitutively shed from the surface of beta-cells, resulting from a degradation of the full-length cellular Tmem27. Overexpression of Tmem27 in a transgenic mouse increases beta-cell mass and improves glucose tolerance in a diet-induced obesity DIO model of diabetes. Furthermore, siRNA knockout of Tmem27 in a rodent beta-cell proliferation assay (e.g. using INS1e cells) reduces the proliferation rate, indicating a role for Tmem27 in control of beta-cell mass.

BACE2 is the protease responsible for the degradation of Tmem27. It is a membrane-bound aspartyl protease and is co-localized with Tmem27 in human pancreatic beta-cells. It is also known to be capable of degrading APP, IL-1R2 and ACE2. The capability to degrade ACE2 indicates a possible role of BACE2 in the control of hypertension.

Inhibitors of BACE1 and/or BACE2 can in addition be used for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmamnn Disease, lupus erythematosus, macrophagic myofasciitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whipple's Disease or Wilson's Disease.

SUMMARY OF THE INVENTION

The present invention is directed to compounds of Formula (I)

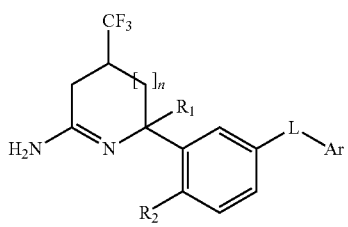

and the tautomers and the stereoisomeric forms thereof, wherein
n is 0 or 1;
$R^1$ is hydrogen, $C_{1-3}$alkyl, cyclopropyl, mono- and polyhalo-$C_{1-3}$alkyl;
$R^2$ is hydrogen or fluoro;
L is a bond or —NHCO—;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy;
heteroaryl is selected from the group consisting of pyridyl, pyrimidyl, pyrazyl, pyridazyl, furanyl, thienyl, pyrrolyl, pyrazolyl, imidazolyl, triazolyl, tetrazolyl, thiazolyl, isothiazolyl, thiadiazolyl, oxazolyl, isoxazolyl, and oxadiazolyl, each optionally substituted with one, two or three substituents selected from the group consisting of halo, cyano, $C_{1-3}$alkyl, $C_{2-3}$alkynyl, $C_{1-3}$alkyloxy, mono- and polyhalo-$C_{1-3}$alkyl, mono- and polyhalo-$C_{1-3}$alkyloxy, and $C_{1-3}$alkyloxy$C_{1-3}$alkyloxy; and the pharmaceutically acceptable acid addition salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described above.

Further exemplifying the invention are methods of inhibiting the beta-secretase enzyme, comprising administering to a subject in need thereof a therapeutically effective amount of any of the compounds or pharmaceutical compositions described above.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease, dementia associated with beta-amyloid, and age-related macular degeneration, preferably Alzheimer's disease, type 2 diabetes and other metabolic disorders, comprising administering to a subject in need thereof, a therapeutically effective amount of any of the compounds or pharmaceutical compositions described above.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease, (i) dementia associated with beta-amyloid or (j) age-related macular degeneration, (k) type 2 diabetes and (l) other metabolic disorders in a subject in need thereof.

DETAILED DESCRIPTION OF THE INVENTION

The present invention is directed to compounds of formula (I) as defined hereinbefore, and pharmaceutically acceptable salts and solvates thereof. The compounds of formula (I) are inhibitors of the beta-secretase enzyme (also known as beta-site cleaving enzyme, BACE, BACE1, Asp2 or memapsin 2, or BACE2), and are useful in the treatment of Alzheimer's disease, mild cognitive impairment, senility, dementia, dementia associated with stroke, dementia with Lewy bodies, Down's syndrome, dementia associated with Parkinson's disease, dementia associated with beta-amyloid, and age-related mamcular degeneration, preferably Alzheimer's disease, mild cognitive impairment or dementia, more preferably Alzheimer's disease, type 2 diabetes and other metabolic disorders.

In an embodiment $R^1$ is methyl.
In an embodiment $R^2$ is hydrogen.
In an embodiment L is —NH—C(═O)—.
In an embodiment Ar is pyridinyl or pyrazinyl substituted with one or two halo atoms or $C_{1-3}$alkyloxy.
In an embodiment $R^1$ is methyl, $R^2$ is hydrogen, L is —NH—C(═O)— and Ar is pyridinyl or pyrazinyl substituted with one or two halo atoms or $C_{1-3}$alkyloxy.
In an embodiment $R^1$ is methyl, $R^2$ is hydrogen, L is —NH—C(═O)— and Ar is 5-methoxypyrazin-2-yl, 5-bromo-pyridin-2-yl, 5-chloro-3-fluoro-pyridin-2-yl or 5-cyano-pyridin-2-yl.
In an embodiment the carbon atom substituted with trifluoromethyl has the R configuration.
In an embodiment $R^2$ is fluoro.
In an embodiment n is 1.
In an embodiment $R^1$ is methyl, $R^2$ is fluoro, n is 1, L is —NH—C(═O)— and Ar is 5-methoxypyrazin-2-yl, 5-chloro-pyridin-2-yl, 5-fluoro-pyridin-2-yl, 5-cyano-pyridin-2-yl, 5-chloro-3-fluoro-pyridin-2-yl or 1-difluoromethyl-pyrazol-3-yl.

In a yet further embodiment, the present invention relates to compounds of Formula (I) as defined hereinbefore wherein the quaternary carbon atom substituted with $R^1$ has a configuration as depicted in the structure (I') below wherein the 2,3,4,5-tetrahydropyridinyl or the 3,4-dihydro-2H-pyrrolyl core is in the plane of the drawing, $R^1$ is projected below the plane of the drawing (with the bond shown with a wedge of parallel lines ⦀) and Ar is projected above the plane of the drawing (with the bond shown with a bold wedge ◀). When $R^1$ is methyl, the quaternary carbon atom has the S-configuration.

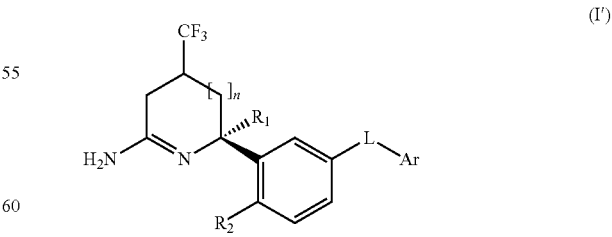

(I')

DEFINITIONS

"Halo" shall denote fluoro, chloro and bromo; "$C_{1-3}$alkyl" shall denote a straight or branched saturated alkyl group having 1, 2 or 3 carbon atoms, e.g. methyl, ethyl, 1-propyl and 2-propyl; "$C_{1-3}$alkyloxy" shall denote an ether radical wherein $C_{1-3}$alkyl is as defined before; "mono- and polyhalo$C_{1-3}$alkyl" shall denote $C_{1-3}$alkyl as defined before, substituted with 1, 2, 3 or where possible with more halo atoms as defined before; "mono- and polyhalo$C_{1-3}$alkyloxy" shall denote an ether radical wherein mono- and polyhalo$C_{1-3}$alkyl is as defined before.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006) or according to the nomenclature rules agreed upon by the International Union of Pure and Applied Chemistry (IUPAC) using Advanced Chemical Development, Inc., software (ACD/Name product version 10.01.0.14105, October 2006). In case of tautomeric forms, the name of the depicted tautomeric form of the structure was generated. The other non-depicted tautomeric form is also included within the scope of the present invention.

The compounds according to formula (I) may be in dynamic equilibrium with their tautomeric form (I*) and form an unseparable mixture. Such tautomeric forms although not explicitly indicated in the above formula are intended to be included within the scope of the present invention.

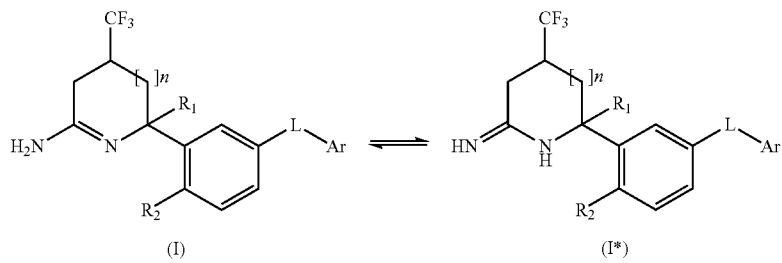

PREPARATION OF THE COMPOUNDS

Experimental Procedure 1

The final compounds according to Formula (I-a) can be prepared by reacting an intermediate compound of Formula (II) with a compound of Formula (III) according to reaction scheme (1), a reaction that is performed in a suitable reaction-inert solvent, such as, for example, N,N-dimethylformamide, in the presence of a suitable base, such as, for example, $K_3PO_4$, a copper catalyst such as, for example, CuI and a diamine such as for example (1R,2R)-(−)-1,2-diaminocyclohexane, under thermal conditions such as, for example, heating the reaction mixture at 180° C., for example for 135 minutes under microwave irradiation. In reaction scheme (1), all variables are defined as in Formula (I) and W is halo.

CAS 148893-10-1] or 4-(4,6-dimethoxy-1,3,5-triazin-2-yl)-4-methylmorpholinium chloride [DMTMM, CAS 3945-69-5], under thermal conditions such as, for example, heating the reaction mixture at 25° C., for example for 2 hours. In reaction scheme (2), all variables are defined as in Formula (I).

Reaction Scheme 2

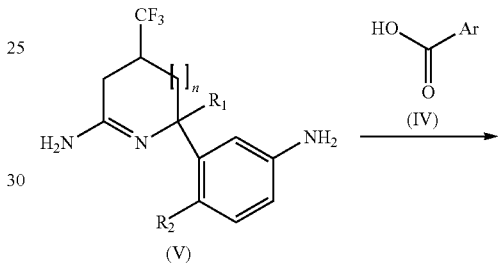

Reaction Scheme 1

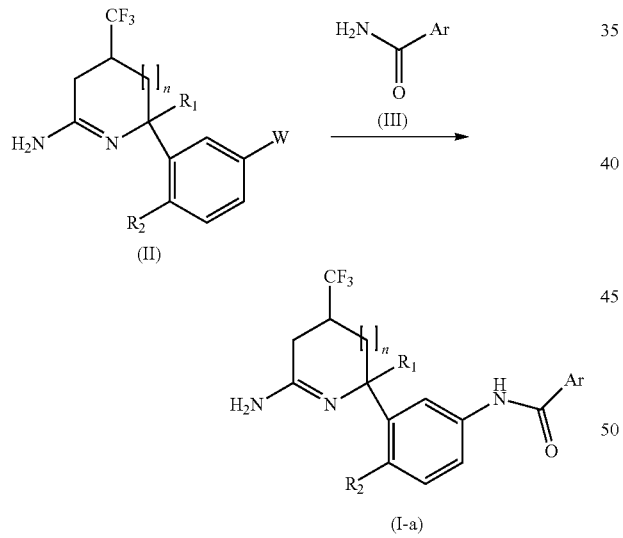

Experimental Procedure 2

Additionally, the final compounds according to Formula (I-a), can be prepared by reacting an intermediate compound of Formula (V) with a compound of Formula (IV) according to reaction scheme (2), a reaction that is performed in a suitable reaction-inert solvent, such as, for example, dichloromethane, in the presence of a suitable base, such as, for example, triethylamine, in the presence of a condensation agent such as for example O-(7azabenzotriazol-1-yl)-N,N,N',N'-tetramethyluronium hexafluorophosphate [HATU,

Experimental Procedure 3

Additionally, the final compounds according to Formula (I-a), can be prepared by reacting an intermediate compound of Formula (V) with a compound of Formula (VI) according to reaction scheme (3), a reaction that is performed in a suitable reaction-inert solvent, such as, for example, dichloromethane, in the presence of a suitable base, such as, for example, pyridine, at room temperature for 2 hours. In reaction scheme (3), all variables are defined as in Formula (I) and Y is halo.

Reaction Scheme 3

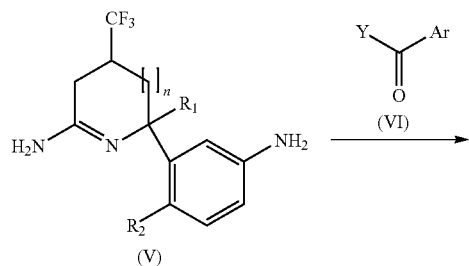

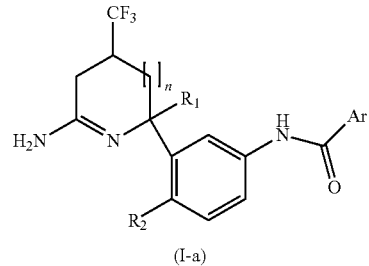

Experimental Procedure 4

The final compounds according to Formula (I-b) can be prepared by reacting an intermediate compound of Formula (II) with a compound of Formula (VII) according to reaction scheme (4), a reaction that is performed in a suitable reaction-inert solvent, such as, for example, 1,4-dioxane, ethanol or mixtures of inert solvents such as, for example, 1,2-dimethoxyethane/water/ethanol or 1,4-dioxane/water, in the presence of a suitable base, such as, for example, aqueous $K_3PO_4$, $NaHCO_3$ or $Cs_2CO_3$, a Pd-complex catalyst such as, for example, [1,1'-bis(diphenylphosphino)ferrocene]dichloropalladium(II) [CAS 72287-26-4] or tetrakis(triphenylphosphine) palladium(0) or trans-bisdicyclohexylamine)palladium diacetate [DAPCy, CAS 628339-96-8] under thermal conditions such as, for example, heating the reaction mixture at 80° C., until completion of the reaction, typically 2-20 hours or for example, heating the reaction mixture at 130° C., for example for 10 minutes under microwave irradiation. In reaction scheme (4), all variables are defined as in Formula (I) and W is halo. $R^3$ and $R^4$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 4

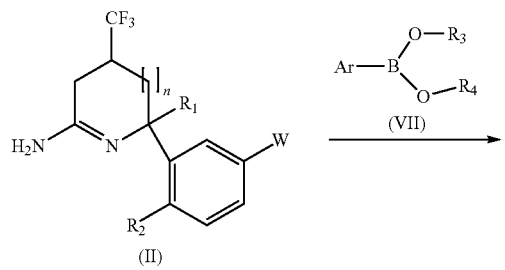

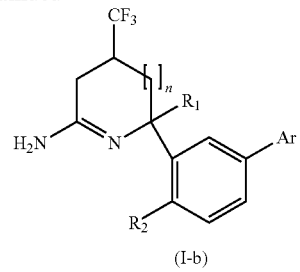

Experimental Procedure 5

The intermediate compounds of Formula (V) and (II) can generally be prepared following the reaction steps shown in the reaction scheme (5) below.

Reaction Scheme 5

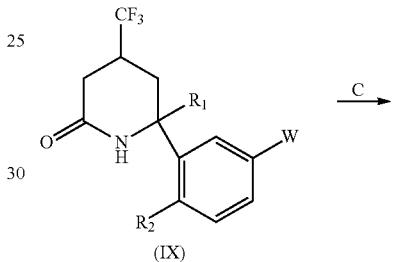

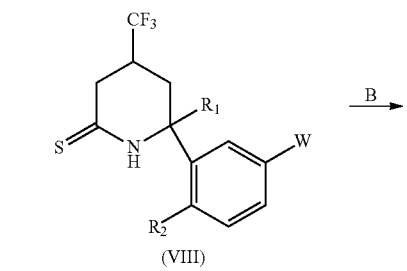

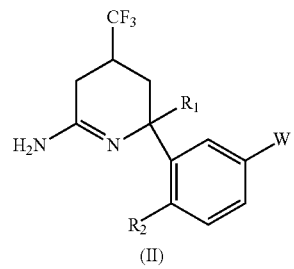

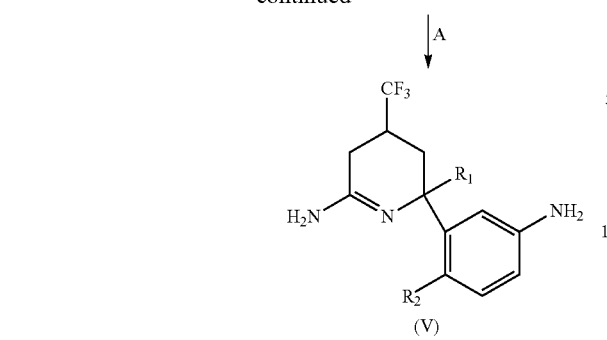

A: Bromo-to-amine conversion
B: thioamide-to-amidine conversion
C: amide-to-thioamide conversion (thionation)

Intermediate compounds of Formula (V) in the above reaction scheme (5) can be prepared from the corresponding intermediate compounds of Formula (II) following art-known copper catalyzed type coupling procedure (reaction step A). Said coupling may be conducted by treatment of said intermediate compounds of Formula (II) with sodium azide in a suitable reaction-inert solvent, such as, for example, DMSO, in the presence of a mixture of suitable bases, such as, for example, dimethylethylenediamine and $Na_2CO_3$, and a copper catalyst such as, CuI, under thermal conditions such as, for example, heating the reaction mixture at 110° C., until completion of the reaction, for example 1 hour.

Intermediate compounds of Formula (II) in the above reaction scheme (5) can be prepared from the corresponding intermediate compounds of Formula (VIII) following art-known thioamide-to-amidine conversion procedures (reaction step B). Said conversion may conveniently be conducted by treatment of intermediate compounds of Formula (VIII) with an ammonia source such as, for example, ammonium chloride or aqueous ammonia, in a suitable reaction-inert solvent such as, for example, water or methanol and the like, under thermal conditions such as, for example, heating the reaction mixture at 60° C., for example for 6 hours.

Intermediate compounds of Formula (VIII) in the above reaction scheme (5) can be prepared from the corresponding intermediate compounds of Formula (IX) following art-known thionation procedures (reaction step C). Said conversion may conveniently be conducted by treatment of intermediate compounds of Formula (IX) with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture at 50° C., for example for 50 minutes.

Experimental Procedure 6

The intermediate compounds of Formula (IX) can generally be prepared following the reaction steps shown in the reaction scheme (6) below.

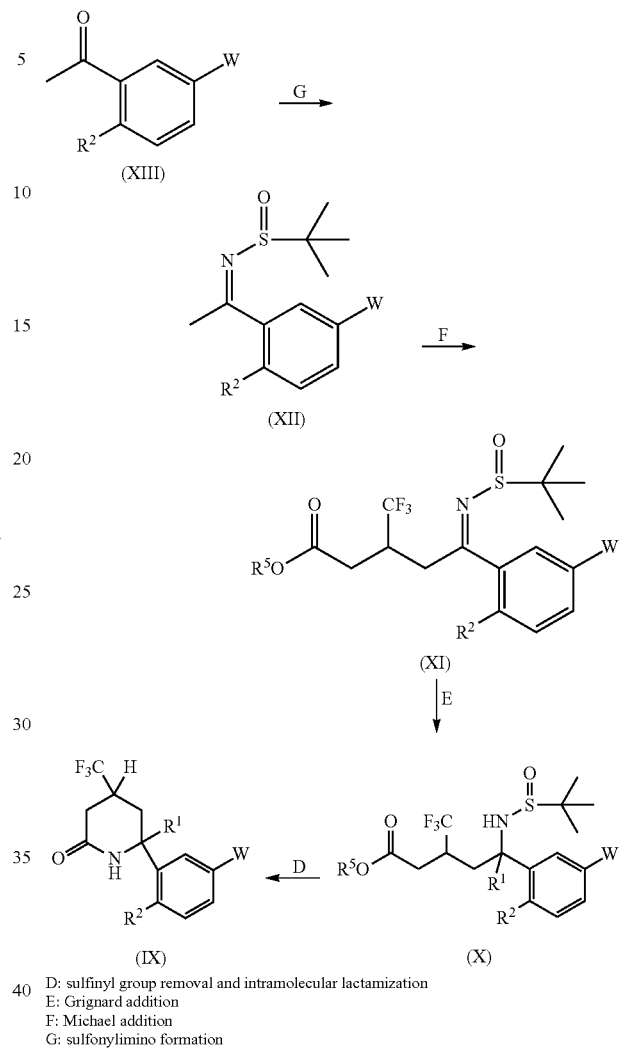

D: sulfinyl group removal and intramolecular lactamization
E: Grignard addition
F: Michael addition
G: sulfonylimino formation Intermediate compound of Formula (IX) in the above reaction scheme (6), can be prepared from intermediate compounds of Formula (X), wherein $R^5$ is $C_{1-4}$ alkyl, by removal of the sulfinyl group followed by intramolecular lactamization (reaction step D). Said conversion can be conducted by treatment of the intermediate of Formula (X) with a suitable acid, such as, for example, hydrochloric acid, in a suitable inert solvent, such as, for example, 1,4-dioxane, at a suitable temperature, for example room temperature for the required time to achieve completion of the reaction, for example 10 minutes. Then intramolecular cyclization is performed by addition of an aqueous base, such as, for example, sodium bicarbonate at a suitable temperature, typically at room temperature until completion of the reaction, for example 30 minutes.

Intermediate compound of Formula (X) wherein $R^5$ is $C_{1-4}$alkyl in the above reaction scheme (6), can be prepared from intermediate compounds of Formula (XI), wherein $R^5$ is $C_{1-4}$alkyl by Grignard addition (reaction step E). Said conversion may be conducted by treatment of an intermediate compound of Formula (XI) with an appropriate Grignard reagent, such as, for example, methylmagnesium bromide, in the presence of a Lewis acid additive, such as, for example, boron trifluoride etherate, in a reaction-inert solvent, such as for example, THF. The reaction mixture is stirred at suitable temperature, for example −78° C. until completion of the reaction, for example 30 minutes.

Intermediate compound of Formula (XI), wherein $R^5$ is $C_{1-4}$alkyl in the above reaction scheme (6), can be prepared from intermediate compounds of Formula (XII) by Michael addition (reaction step F). Said conversion may be conducted by treatment of an intermediate compound of Formula (XII) with an appropriate Michael acceptor, such as, for example, ethyl (2E)-4,4,4-trifluorobut-2-enoate, and a suitable base, such as, for example, potassium tert-butoxide, in a reaction-inert solvent, such as, for example, THF. The reaction mixture is stirred at suitable temperature, for example −30° C. until completion of the reaction, for example one hour.

Intermediate compounds of Formula (XII) in the above reaction scheme (6), can be prepared by the reaction between an intermediate compound of Formula (XIII) and tert-butylsulfinamide (reaction step G), in a suitable reaction-inert solvent, such as, for example, heptane or THF in the presence of a suitable Lewis acid, such as, for example, titanium tetraethoxide, under thermal conditions such as, for example, heating the reaction mixture at 70° C., for example for a period of 16 hours.

In reaction scheme (6), all variables are defined as in Formula (I), $R^5$ is $C_{1-4}$ alkyl and W is halo.

Intermediate compounds of Formula (XIII) are commercially available or can be synthesized by art-known reaction procedures.

Experimental Procedure 7

The intermediate compounds of Formula (XIV) can generally be prepared following the reaction steps shown in the reaction scheme (7) below.

Reaction Scheme 7

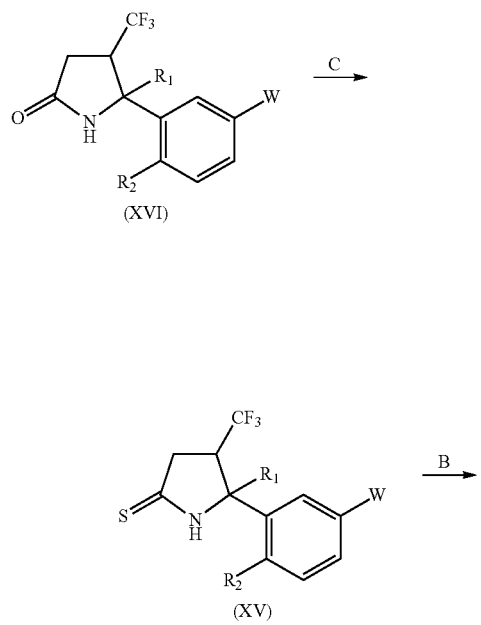

(XVI)

(XV)

-continued

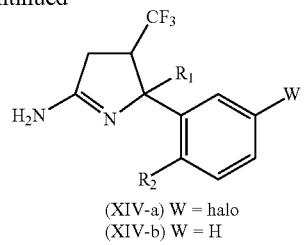

(XIV-a) W = halo
(XIV-b) W = H

B: thioamide-to-amidine conversion
C: amide-to-thioamide conversion (thionation)

Intermediate compounds of Formula (XIV-a or b) in the above reaction scheme (7) can be prepared from the corresponding intermediate compounds of Formula (XV) following art-known thioamide-to-amidine conversion procedures (reaction step B). Said conversion may conveniently be conducted by treatment of intermediate compounds of Formula (XV) with an ammonia source such as, for example, ammonium chloride or aqueous ammonia, in a suitable reaction-inert solvent such as, for example, water or methanol and the like, under thermal conditions such as, for example, heating the reaction mixture at 60° C., for example for 6 hours, or heating the reaction under microwave irradiation at 120° C. during 1 hour.

Intermediate compounds of Formula (XV) in the above reaction scheme (7) can be prepared from the corresponding intermediate compounds of Formula (XVI) following art-known thionation procedures (reaction step C). Said conversion may conveniently be conducted by treatment of intermediate compounds of Formula (XVI) with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture at 50° C., for example for 2 hours.

In reaction scheme (7), all variables are defined as in Formula (I) and W is halo or hydrogen.

Experimental Procedure 8

The intermediate compounds of Formula (XVII) can generally be prepared following the reaction steps shown in the reaction scheme (8) below.

Reaction Scheme 8

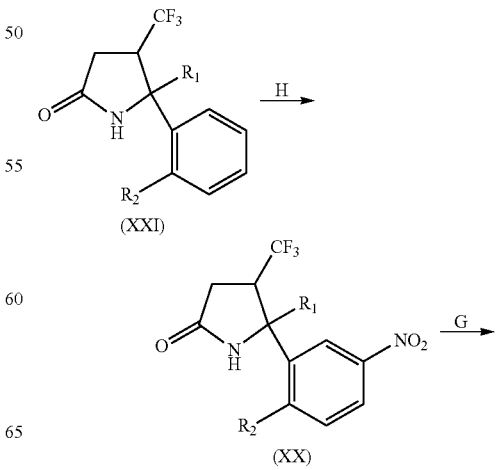

(XXI)

(XX)

-continued

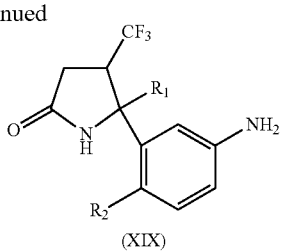

(XIX)

↓C

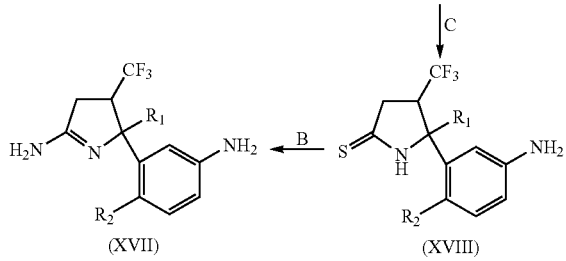

(XVII)    (XVIII)

B: thioamide-to-amidine conversion
C: amide-to-thioamide conversion (thionation)
G: nitro-to-amino reduction
H: nitration Intermediate compounds of Formula (XVII) in the above reaction scheme (8) can be prepared from the corresponding intermediate compounds of Formula (XVIII) following art-known thioamide-to-amidine conversion procedures (reaction step B). Said conversion may conveniently be conducted by treatment of intermediate compounds of Formula (XVIII) with an ammonia source such as, for example, ammonium chloride or aqueous ammonia, in a suitable reaction-inert solvent such as, for example, water or methanol and the like, under thermal conditions such as, for example, heating the reaction mixture at 60° C., for example for 6 hours, or heating the reaction under microwave irradiation at 120° C. during 1 hour.

Intermediate compounds of Formula (XVIII) in the above reaction scheme (8) can be prepared from the corresponding intermediate compounds of Formula (XIX) following art-known thionation procedures (reaction step C). Said conversion may conveniently be conducted by treatment of intermediate compounds of Formula (XIX) with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture at 50° C., for example for 2 hours.

Intermediate compounds of Formula (XIX) can be prepared from the corresponding intermediates of Formula (XX) following art-known nitro-to-amino reduction procedures (reaction step G) according to reaction scheme (8). Said reduction may conveniently be conducted following art-known catalytic hydrogenation procedures. For example, said reduction may be carried out by stirring the intermediate compounds of Formula (XX) under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageously to elevate the temperature and/or the pressure of the reaction mixture.

Intermediates compounds of Formula (XX) can be prepared from the corresponding intermediates of Formula (XXI) following art-known nitration procedures (reaction step H) according to reaction scheme (8). Said nitration may conveniently be conducted by treatment of the corresponding intermediate compounds of Formula (XXI) with a nitrating agent such as, for example, nitric acid in the presence of a suitable protonating agent such as, for example, sulfuric acid at moderate temperature such as, for example, 25° C., for example for 2 hours.

In reaction scheme (8), all variables are defined as in Formula (I).

Experimental Procedure 9

The intermediate compounds of Formula (XXII) can generally be prepared following the reaction steps shown in the reaction scheme (9) below.

Reaction Scheme 9

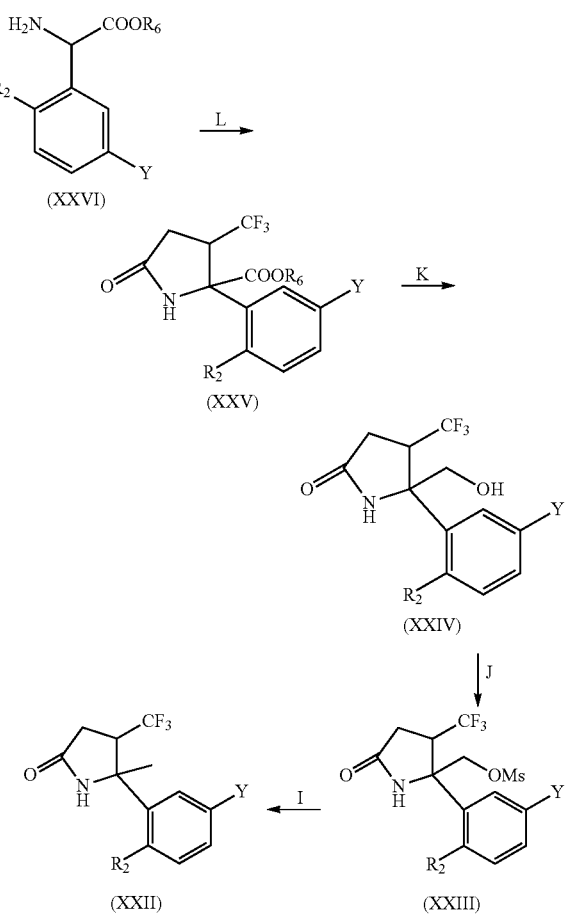

I: mesylate-to-methyl conversion
J: alcohol-to-mesylate conversion
K: ester-to-alcohol reduction
L: Michael addition and intramolecular lactamization Intermediate compounds of Formula (XXII) in the above reaction scheme (9) can be prepared from the corresponding intermediate compounds of Formula (XXIII) following art-known mesylate-to-methyl conversion procedures (reaction step I). Said conversion may conveniently be conducted by treatment of intermediate compounds of Formula (XXIII) with a reducing agent such as, for example, sodium borohydride or lithium aluminium hydride, in a reaction inert solvent such as, for example, dimethylformamide or tetrahydrofuran and the like, under thermal conditions such as, for example, heating the reaction mixture at 70° C., for example for 4 hours.

Intermediate compounds of Formula (XXIII) in the above reaction scheme (9) can be prepared from the corresponding intermediate compounds of Formula (XXIV) following art-known alcohol-to-mesylate conversion procedures (reaction step J). Said conversion may conveniently be conducted by treatment of intermediate compounds of Formula (XXIV) with a suitable reagent such as, for example, methanesulfonyl chloride, in a reaction inert solvent such as, for example, dichloromethane, in the presence of a suitable base, such as, triethylamine, at a moderate temperature such as, for example, 0° C., for 2 hours.

Intermediate compounds of Formula (XXIV) can be prepared from the corresponding intermediates of Formula (XXV) following art-known ester-to-alcohol reduction procedures (reaction step K) according to reaction scheme (9). Said reduction may conveniently be conducted by treatment of intermediate compounds of Formula (XXV) with a suitable reducing agent such as, for example, sodium borohydride, in a suitable solvent such as, for example, tetrahydrofuran and the like, or mixtures of solvents such as, for example tetrahydrofuran and water. Reaction may be carried out at a moderate temperature such as, for example 0° C. for 2 hours.

Intermediate compound of Formula (XXV) in the above reaction scheme (9), can be prepared from intermediate compounds of Formula (XXVI) by Michael addition followed by intramolecular lactamization (reaction step L). Said conversion may be conducted by treatment of an intermediate compound of Formula (XXVI) with an appropriate Michael acceptor, such as, for example, ethyl (2E)-4,4,4-trifluorobut-2-enoate, and a suitable base, such as, for example, sodium hydride, in a reaction-inert solvent, such as for example, THF. The reaction mixture is stirred at suitable temperature, for example 0° C. until completion of the reaction, for example 6 hours.

In reaction scheme (9), all variables are defined as in Formula (I), Y is halo or hydrogen and $R_6$ is methyl or ethyl.

Experimental Procedure 10

Alternatively, intermediate compounds of Formula (XVII) can be prepared following the reaction steps shown in the reaction scheme (10) below.

Reaction Scheme 10

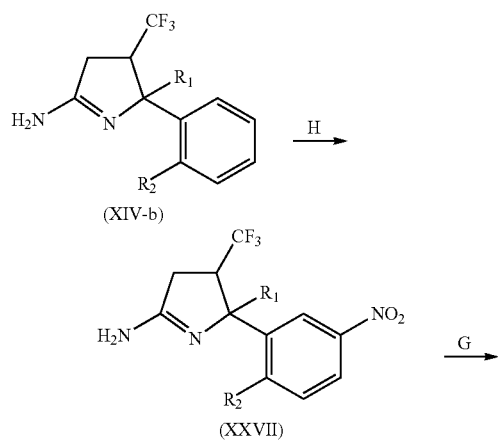

-continued

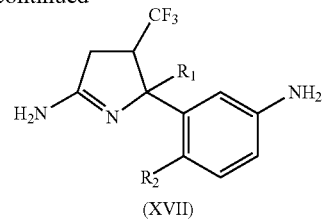

G: nitro-to-amino reduction
H: nitration

Intermediate compounds of Formula (XVII) can be prepared from the corresponding intermediates of Formula (XXVII) following art-known nitro-to-amino reduction procedures (reaction step G) according to reaction scheme (10). Said reduction may conveniently be conducted following art-known catalytic hydrogenation procedures. For example, said reduction may be carried out by stirring the intermediate compounds of Formula (XXVII) under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture.

Intermediates compounds of Formula (XXVII) can be prepared from the corresponding intermediates of Formula (XIV-b) following art-known nitration procedures (reaction step H) according to reaction scheme (10). Said nitration may conveniently be conducted by treatment of the corresponding intermediate compounds of Formula (XIV-b) with a nitrating agent such as, for example, nitric acid in the presence of a suitable protonating agent such as, for example, sulfuric acid at moderate temperature such as, for example, 0° C., for example for 30 minutes.

In reaction scheme (10), all variables are defined as in Formula (I).

Pharmacology

The compounds of the present invention and the pharmaceutically acceptable compositions thereof inhibit BACE and therefore may be useful in the treatment or prevention of Alzheimer's Disease (AD), mild cognitive impairment (MCI), senility, dementia, dementia with Lewy bodies, cerebral amyloid angiopathy, multi-infarct dementia, Down's syndrome, dementia associated with Parkinson's disease, dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid and age-related and age-related macular degeneration, type 2 diabetes and other metabolic disorders.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

The invention also relates to a compound according to the general Formula (I), a stereoisomeric form thereof or a the pharmaceutically acceptable acid or base addition salt thereof, for use in the treatment or prevention of diseases or conditions selected from the group consisting of AD, MCI, senility, dementia, dementia with Lewy bodies, cerebral amyloid angiopathy, multi-infarct dementia, Down's syndrome, dementia associated with Parkinson's disease, dementia of the Alzheimer's type, dementia associated with beta-amyloid and age-related macular degeneration, type 2 diabetes and other metabolic disorders.

The invention also relates to a compound according to the general Formula (I), a stereoisomeric form thereof or a the pharmaceutically acceptable acid or base addition salt thereof, for use in the treatment, prevention, amelioration, control or reduction of the risk of diseases or conditions selected from the group consisting of AD, MCI, senility, dementia, dementia with Lewy bodies, cerebral amyloid angiopathy, multi-infarct dementia, Down's syndrome, dementia associated with Parkinson's disease, dementia of the Alzheimer's type, dementia associated with beta-amyloid and age-related macular degeneration, type 2 diabetes and other metabolic disorders.

As already mentioned hereinabove, the term "treatment" does not necessarily indicate a total elimination of all symptoms, but may also refer to symptomatic treatment in any of the disorders mentioned above. In view of the utility of the compound of Formula (I), there is provided a method of treating subjects such as warm-blooded animals, including humans, suffering from or a method of preventing subjects such as warm-blooded animals, including humans, suffering from any one of the diseases mentioned hereinbefore.

Said methods comprise the administration, i.e. the systemic or topical administration, preferably oral administration, of a therapeutically effective amount of a compound of Formula (I), a stereoisomeric form thereof, a pharmaceutically acceptable addition salt or solvate thereof, to a subject such as a warm-blooded animal, including a human.

Therefore, the invention also relates to a method for the prevention and/or treatment of any of the diseases mentioned hereinbefore comprising administering a therapeutically effective amount of a compound according to the invention to a subject in need thereof.

A method for modulating beta-site amyloid cleaving enzyme activity, comprising administering to a subject in need thereof, a therapeutically effective amount of a compound according to claim 1 or a pharmaceutical composition according to claim 10.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

A skilled person will be familiar with alternative nomenclatures, nosologies, and classification systems for the diseases or conditions referred to herein. For example, the fifth edition of the Diagnostic & Statistical Manual of Mental Disorders (DSM-5™) of the American Psychiatric Association utilizes terms such as neurocognitive disorders (NCDs) (both major and mild), in particular, neurocognitive disorders due to Alzheimer's disease, due to traumatic brain injury (TBI), due to Lewy body disease, due to Parkinson's disease or to vascular NCD (such as vascular NCD present with multiple infarctions). Such terms may be used as an alternative nomenclature for some of the diseases or conditions referred to herein by the skilled person.

Pharmaceutical Compositions

The present invention also provides compositions for preventing or treating diseases in which inhibition of beta-secretase is beneficial, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid and age-related macular degeneration, type 2 diabetes and other metabolic disorders. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage.

Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area. A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

Experimental Part

Hereinafter, the term "m.p." means melting point, "min" means minutes, "aq." means aqueous, "r.m." means reaction mixture, "r.t." means room temperature, "THF" means tetrahydrofuran, "DMF" means dimethylformamide, "DCM" means dichloromethane, "EtOAc" means ethyl acetate, "MeCN" means acetonitrile, "MeOH" means methanol, "rac" means racemic, "sat." means saturated, "SFC" means supercritical fluid chromatography, "SFC-MS" means supercritical fluid chromatography/mass spectrometry, "LC-MS" means liquid chromatography/mass spectrometry, "GCMS" means gas chromatography/mass spectrometry, "HPLC" means high-performance liquid chromatography, "RP" means reversed phase, "UPLC" means ultra-performance liquid chromatography, "$R_t$" means retention time (in minutes), "[M+H]+" means the protonated mass of the free base of the compound, "DMTMM" means 4-(4,6-dimethoxy-1,3,5-triazin-2-yl)-4-methylmorpholinium chloride, "$Et_2O$" means diethylether, "DMSO" means dimethylsulfoxide, "NMR" means nuclear magnetic resonance, "LDA" means lithium diisopropylamide, "$NH_4Cl$" means ammonium chloride, "$MgSO_4$" means magnesium sulfate, "$NaHCO_3$" means ammonium bicarbonate, "HCl" means hydrochloric acid, "$P_2S_5$" means phosphorus pentasulfide, "$Na_2SO_4$" means sodium sulfate, "$CO_2$" means carbon dioxide, "$iPrNH_2$" means isopropyl amine, "$NH_4HCO_3$" means ammonium hydrogenocarbonate, "iPrOH" means isopropanol, "EtOH" means ethanol and "wt" means weight.

For key intermediates, as well as some final compounds, the absolute configuration of chiral centers (indicated as R and/or S) were established via comparison with samples of known configuration, or the use of analytical techniques suitable for the determination of absolute configuration, such as VCD (vibrational cicular dichroism) or X-ray crystallography.

A. Preparation of the Intermediates

Example A1

Preparation of Intermediate 1

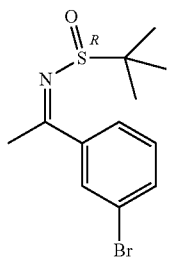

Titanium(IV) isopropoxide (65 g, 286 mmol) was added to a stirred mixture of 3-bromoacetophenone [(CAS 2142-63-4), 30 g, 150 mmol] and (R)-2-methyl-2-propanesulfinamide (21.9 g, 181 mmol) in THF (600 mL). The mixture was stirred at 80° C. for 16 hours. The mixture was cooled to r.t., and water was added. The resulting mixture was filtered over a diatomaceous earth pad. The filtrate was extracted with EtOAc (3×). The combined organic layers were dried (MgSO$_4$), filtered and concentrated in vacuo. The residue was purified by flash column chromatography (silica gel; eluent: heptane/EtOAc 100/0 to 75/25). The desired fractions were collected and concentrated in vacuo to yield intermediate 1 (38 g, 79% yield) as a yellow oil.

Example A2

Preparation of Intermediate 2

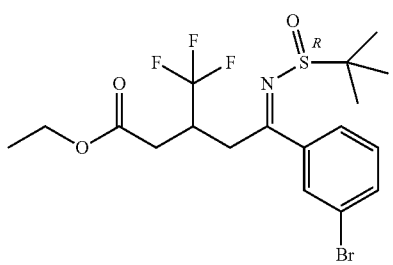

Intermediate 1 (20.6 g, 68 mmol) and ethyl (2E)-4,4,4-trifluorobut-2-enoate (10.2 mL, 68 mmol) were dissolved in THF (950 mL) and cooled down to −30° C. under nitrogen. Potassium tert-butoxide (15.3 g, 136 mmol) was added while keeping the temperature at −30° C. After one hour, the reaction was quenched using sat. aq. NH$_4$Cl solution (110 mL) and the mixture was allowed to warm to r.t. The mixture was extracted with DCM (3×) and washed with brine (2×). The combined organic layers were dried (MgSO$_4$), filtered and the solvents evaporated in vacuo. The residue was purified by flash column chromatography (silica gel; eluent:

heptane/EtOAc 100/0 to 80/20). The desired fractions were collected and concentrated in vacuo to yield intermediate 2 (15.77 g, 46% yield).

Example A3

Preparation of Intermediate 3

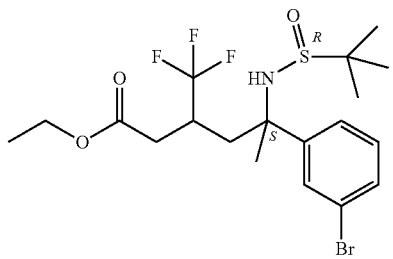

Boron trifluoride etherate (17.6 mL, 67 mmol) was added dropwise to a stirred solution of intermediate 2 (15.8 g, 33.5 mmol) in THF (327 mL) at −78° C. under nitrogen. After 5 min, methylmagnesium bromide (1.4 M, 120 mL, 167.6 mmol) was added and the mixture was stirred at −78° C. for 30 min. The reaction was quenched with sat. aq. NaHCO$_3$ solution (120 mL) and the mixture was extracted with DCM (3×). The combined organic layers were dried (MgSO$_4$), filtered and the solvents evaporated in vacuo. The residue was purified by flash column chromatography (silica gel; eluent: heptane/EtOAc 90/10 to 60/40). The desired fractions were collected and concentrated in vacuo to yield intermediate 3 (8.23 g, 50% yield).

Example A4

Preparation of Intermediate 4

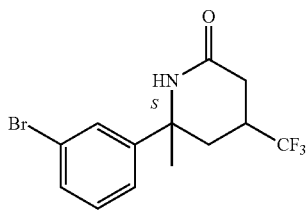

HCl (4M solution in dioxane, 32 mL, 128 mmol) was added slowly to intermediate 3 (8.23 g, 14.2 mmol) and the mixture was stirred at r.t. for 10 min. The r.m. was concentrated in vacuo and the residue was dissolved in DCM (100 mL). Sat. aq. NaHCO$_3$ solution was added until pH 8 and the r.m. was stirred for 30 min. The mixture was extracted with DCM (3×) and the combined organic layers were dried (MgSO$_4$), filtered and the solvents evaporated in vacuo. The residue was purified by flash column chromatography (silica gel; eluent: heptane/EtOAc 100/0 to 45/55). The desired fractions were collected and concentrated in vacuo to yield intermediate 4 (5.26 g, 93% yield) as a mixture of diastereomers.

Example A5

Preparation of Intermediate 5

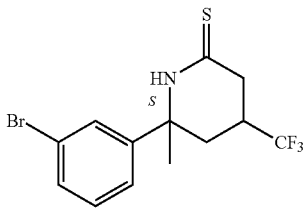

P$_2$S$_5$ (2.92 g, 13.14 mmol) was added to a solution of intermediate 4 (5.26 g, 13.14 mmol) in THF (50 mL) at r.t. The mixture was stirred at 60° C. for 45 min, then cooled to r.t., filtered off and the organic solvent evaporated in vacuo. The crude product was purified by flash column chromatography (silica gel; eluent: DCM). The desired fractions were collected and evaporated in vacuo to yield intermediate 5 (3.94 g, 85% yield) as a mixture of diastereomers (3:1).

Example A6

Preparation of Intermediate 6

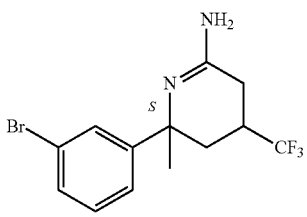

Intermediate 5 (1.67 g, 4.74 mmol) was dissolved in 7N ammonia in MeOH (153 mL) and the r.m. was stirred at 90° C. for 16 hours. The solvent was then evaporated and the crude product was purified by column chromatography (silica gel; eluent: DCM/7M solution of ammonia in MeOH 100/0 to 90/10). The desired fractions were collected and concentrated in vacuo to yield intermediate 6 (1.46 g, 92% yield, mixture of diastereomers) as a brownish oil.

Example A7

Preparation of Intermediate 7

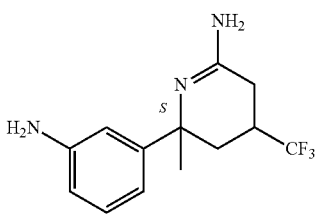

Intermediate 6 (1 g, 2.98 mmol) was combined with sodium azide (0.485 g, 7.46 mmol), copper iodide (0.71 g, 5.22 mmol) and sodium carbonate (0.632 g, 5.97 mmol) in DMSO (43 mL) and the reaction was degassed. After that, N,N'-dimethylethylene-diamine (0.56 mL, 5.22 mmol) was added and the mixture was heated at 110° C. until completion of the reaction. The r.m. was cooled down and DCM was added. The organic layer was washed with aq. ammonia solution. The organic layer was separated, dried (MgSO$_4$), filtered and concentrated in vacuo. The crude product was purified by column chromatography (silica gel; eluent: DCM/7M solution of ammonia in MeOH 100/0 to 80/20). The desired fractions were collected and concentrated in vacuo to yield intermediate 7 (0.271 g, 31% yield, mixture of diastereomers).

Example A8

Preparation of Intermediate 8.1

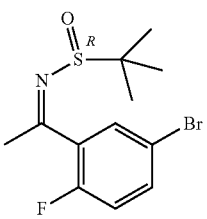

Titanium(IV) isopropoxide (126 g, 552.99 mmol) was added to a stirred mixture of 5-bromo-2-fluoroacetophenone [(CAS 198477-89-3), 120 g, 552.99 mmol] and (R)-2-methyl-2-propanesulfinamide (67 g, 552.99 mmol) in THF (600 mL). The mixture was stirred at 80° C. for 16 hours. The mixture was cooled down to r.t., and water was added. The resulting mixture was filtered over a diatomaceous earth pad. The filtrate was extracted with EtOAc (3×). The combined organic layers were dried (MgSO$_4$), filtered and concentrated in vacuo. The residue was purified by flash column chromatography (silica gel; eluent: petroleum ether/EtOAc 51/0 to 50/1). The desired fractions were collected and concentrated in vacuo to yield intermediate 8 (100 g, 57% yield).

Example A9

Preparation of Intermediate 9

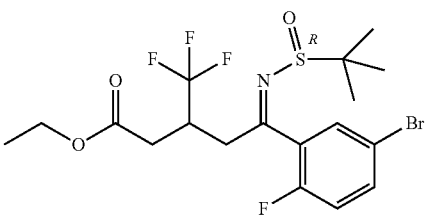

Intermediate 8 (100 g, 312.5 mmol) and ethyl (2E)-4,4,4-trifluorobut-2-enoate (53 g, 312.5 mmol) were dissolved in THF (500 mL) and cooled down to −78° C. under nitrogen. LDA solution (625 mL, 312.5 mmol) was added while keeping the temperature at −78° C. After full conversion, the reaction was quenched using sat. aq. NH$_4$Cl solution (300 mL) and the mixture was allowed to warm to r.t. The mixture was extracted with DCM (3×) and washed with brine (2×). The combined organic layers were dried (MgSO₄), filtered and the solvents evaporated in vacuo to yield intermediate 9 (100 g, 81% yield), which was used as such in the next reaction.

Example A10

Preparation of Intermediate 10

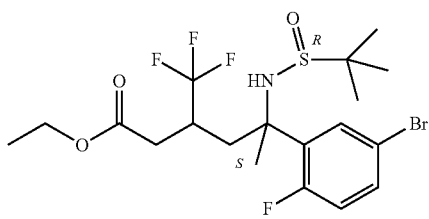

Intermediate 10 was prepared following a synthetic procedure similar to the one reported for the synthesis of intermediate 3. Starting from intermediate 9 (120 g, 245.9 mmol) intermediate 10 was obtained and used as such in the next step (100 g, 80% yield).

Example A11

Preparation of Intermediate 11

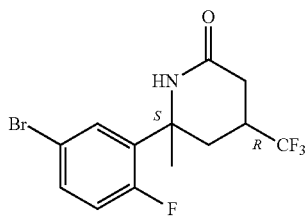

Intermediate 11 was prepared following a synthetic procedure similar to the one reported for the synthesis of intermediate 4. Starting from intermediate 10 (100 g, 198.4 mmol) intermediate 11 was obtained (8.1 g, 12% yield).

Example A12

Preparation of Intermediate 12

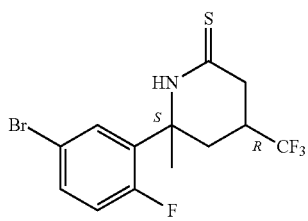

Intermediate 12 was prepared following a synthetic procedure similar to the one reported for the synthesis of intermediate 5. Starting from intermediate 11 (8 g, 18.98 mmol) intermediate 12 was obtained as a white powder (5.53 g, 79% yield).

Example A13

Preparation of Intermediate 13

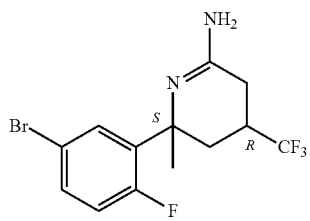

Intermediate 12 (5.53 g, 14.94 mmol) was dissolved in 7N ammonia in MeOH (482 mL) and the r.m. was stirred at 90° C. for 16 hours, then the solvent was evaporated and the crude product was redissolved in 7N ammonia in MeOH (482 mL) and the r.m. was stirred at 90° C. for another 24 hours until full conversion. The solvent was evaporated and the crude product was purified by column chromatography (silica gel; eluent: DCM/7M ammonia in MeOH 100/0 to 90/10). The desired fractions were collected and concentrated in vacuo to yield intermediate 13 (5.073 g, 96% yield) as a brownish oil.

Example A14

Preparation of Intermediate 14

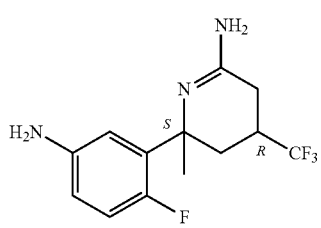

Intermediate 14 was prepared following a synthetic procedure similar to the one reported for the synthesis of intermediate 7. Starting from intermediate 13 (5.073 g, 14.37 mmol) intermediate 14 was obtained as a light brown oil.

Example A15

Preparation of Intermediate 15

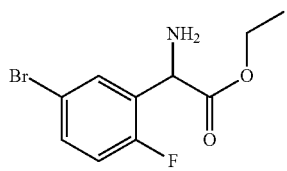

Thionyl chloride (19.9 mL, 274.14 mmol) was added to a mixture of 2-amino-2-(5-bromo-2-fluorophenyl)acetic acid (CAS: 318269-93-1, 20 g, 80.63 mmol) in EtOH (264 mL) at 0° C. The mixture was refluxed for 16 h, then the volatiles were removed in vacuo and the crude product was diluted with sat. aq. NaHCO₃ solution. The product was extracted with DCM. The organic layer was dried over Na₂SO₄, filtered and concentrated in vacuo to yield a yellow oil, which was purified by column chromatography (silica gel; eluent: heptane/EtOAc 100/0 to 50/50). The desired fractions were collected and concentrated in vacuo to intermediate 15 (14.22 g, 64%) as a yellow oil.

Example A16

Preparation of Intermediate 16

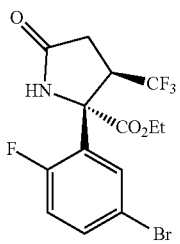 [SMILES: CCOC(=O)[C@]1(c2cc(Br)ccc2F)NC(=O)C[C@H]1C(F)(F)F]

NaH (60% dispersion in mineral oil, 6.08 g, 152.06 mmol) was added to a solution of intermediate 15 (13 g, 47.08 mmol) in THF (310 mL) cooled at 0° C. After stirring for 20 minutes, ethyl 4,4,4-trifluorocrotonate (24.7 mL, 164.79 mmol) was added dropwise and the mixture was stirred for 2 hours. The mixture was then diluted with water and the aq. layer was extracted with EtOAc. The organic layer was separated, dried over Na₂SO₄, filtered and the solvents removed in vacuo to yield a yellow solid, further purified by column chromatography (silica gel; heptane/ EtOAc 100/0 to 60/40). The desired fractions were collected and concentrated in vacuo to yield intermediate 16 (13.4 g, 71%, racemic mixture) as a yellow solid.

Example A17

Preparation of Intermediate 17

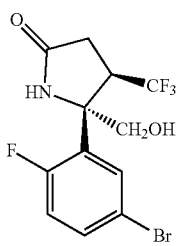 [SMILES: O=C1C[C@@H](C(F)(F)F)[C@@](CO)(c2cc(Br)ccc2F)N1]

Sodium borohydride (7.127 g, 188.37 mmol) was added in several portions to a solution of intermediate 16 (15 g, 37.674 mmol) in a mixture of THF (344 mL) and water (26 mL) cooled at 0° C. The mixture was stirred for 5 hours, then it was diluted with sat. aq. NH₄Cl solution and the aq. layer was extracted with EtOAc. The organic layer was separated, dried over Na₂SO₄, filtered and the solvents concentrated in vacuo. The crude product was purified by column chromatography (silica gel; hexane/EtOAc 100/100 to 30/70). The desired fractions were collected and concentrated in vacuo to yield intermediate 17 (11.66 g, 87%, racemic mixture) as a white solid.

By using reaction conditions similar to the ones reported for the synthesis of intermediate 16 and intermediate 17, intermediate 17 may be as well obtained in two steps starting from commercially available methyl 2-amino-2-(5-bromo-2-fluorophenyl)acetate (CAS:1218158-22-5).

Example A18

Preparation of Intermediate 18

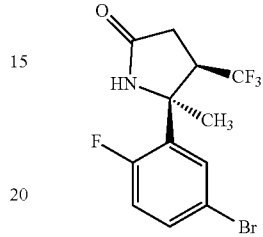

Methanesulfonyl chloride (0.26 mL, 3.37 mmol) and triethylamine (0.47 mL, 3.37 mmol) were added to a solution of intermediate 17 (400 mg, 1.12 mmol) in DCM (10 mL) cooled at 0° C. and the mixture was stirred for 2 hours. The mixture was diluted with sat. aq. NH₄Cl solution and the aq. layer was extracted with EtOAc (3×). The organic layer was separated, dried over Na₂SO₄, filtered and the solvents concentrated in vacuo. The crude was dissolved in DMF (10 mL) and sodium borohydride (128 mg, 3.37 mmol) was added. The mixture was heated at 70° C. for 4 hours. The mixture was diluted with water and the aq. layer was extracted with EtOAc (3×). The organic layer was separated, dried over Na₂SO₄, filtered and the solvents concentrated in vacuo. The crude product was purified by column chromatography (silica gel; eluent: heptane/EtOAc 50/50 to 0/100) to afford intermediate 18 (220 mg, 58% yield, racemic mixture) as a solid (m.p. 166-168° C.).

Example A19

Preparation of Intermediate 19

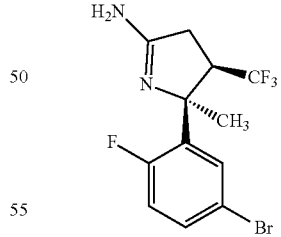

P₂S₅ (89 mg, 0.40 mmol) was added to a solution of intermediate 18 (170 mg, 0.50 mmol) in THF (5 mL) and the mixture was heated at 50° C. for 2 hours. The resulting suspension was filtered and the filtrate was concentrated at reduced pressure. The crude product was dissolved in 7M solution of ammonia in MeOH (1 mL) and 32% aq. ammonia solution (2.5 mL) was added. The mixture was heated for 1 hour at 120° C. under microwave irradiation, then it was diluted with water and extracted with DCM (3×). The organic layer was separated, dried over Na₂SO₄, filtered and the solvents concentrated in vacuo. The crude product was purified by column chromatography (silica gel; eluent: EtOAc/Hexane/7M solution of ammonia in MeOH 30/90/10) to afford intermediate 19 (105 mg, 62% yield, racemic mixture) as a solid (m.p. 110-112° C.).

Example A20

Preparation of Intermediate 20

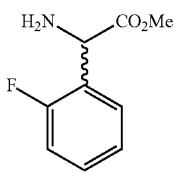

Thionyl chloride (1.27 mL, 17.4 mmol) was added dropwise to a suspension of 2-amino-2-(2-fluorophenyl)acetic acid [(CAS 84145-28-8), 2.26 g, 13.37 mmol] in MeOH (45 mL) and the mixture was refluxed for 18 hours. The mixture was then concentrated in vacuo, the crude product was suspended in DCM (45 mL) and triethylamine (3.72 mL, 26.7 mmol) was added. The mixture was stirred at r.t. for 10 min and then concentrated in vacuo. The crude product was suspended in Et₂O, the precipitate was removed by filtration and the filtrate was concentrated in vacuo to afford intermediate 20 (2.35 g, 96% yield, racemic mixture).

Example A21

Preparation of Intermediate 21 and Intermediate 22 intermediate 21

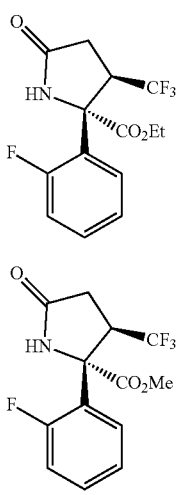

intermediate 22

Sodium hydride (60% in mineral oil, 1.31 g, 32.75 mmol) was added to a solution of intermediate 20 (2 g, 10.92 mmol) in THF (109 mL) cooled at 0° C. After stirring for 20 min, ethyl (2E)-4,4,4-trifluorobut-2-enoate (5.71 mL, 38.22 mmol) was added dropwise and the mixture was stirred for 6 hours. The mixture was diluted with water and the aq. layer was extracted with EtOAc (3×). The organic layer was separated, dried over Na₂SO₄, filtered and the solvents concentrated in vacuo. The crude product was purified by column chromatography (silica gel; eluent: heptane/EtOAc 50/50). The desired fractions were collected and concentrated in vacuo to afford intermediate 21 (1.36 g, 39% yield, racemic mixture) and intermediate 22 (765 mg, 23% yield, racemic mixture) both as white solids (intermediate 21, m.p. 161-163° C.; intermediate 22, m.p. 182-184 PC).

Example A22

Preparation of Intermediate 23

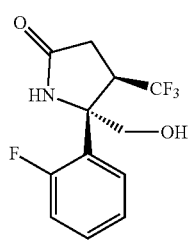 [SMILES: O=C1C[C@@H](C(F)(F)F)[C@@](CO)(c2ccccc2F)N1]

Sodium borohydride (340 mg, 9.0 mmol) was added in several portions to a solution of intermediate 22 (550 mg, 1.80 mmol) in a mixture of THF:water (18:1.5 mL) cooled at 0° C. and the mixture was stirred 2 hours. The mixture was diluted with sat. aq. sol. of NH₄Cl and the aq. layer was extracted with EtOAc (3×). The organic layer was separated, dried over Na₂SO₄, filtered and the solvents concentrated in vacuo. The crude product was purified by column chromatography (silica gel; eluent: heptane/EtOAc 70/30). The desired fractions were collected and concentrated in vacuo to afford intermediate 23 (490 mg, 98% yield, racemic mixture) as a solid (m.p. 170-172° C.).

Example A23

Preparation of Intermediate 24

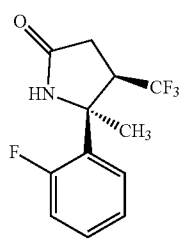

Methanesulfonyl chloride (0.39 mL, 5.1 mmol) and triethylamine (0.71 mL, 5.1 mmol) were added to a solution of intermediate 23 (470 mg, 1.69 mmol) in DCM (17 mL) cooled at 0° C. and the mixture was stirred for 2 hours. The mixture was diluted with sat. aq. NH₄Cl solution and the aq. layer was extracted with EtOAc (3×). The organic layer was separated, dried over Na₂SO₄, filtered and the solvents concentrated in vacuo. The crude was dissolved in DMF (17 mL), sodium borohydride (192 mg, 5.07 mmol) was added and the mixture was heated at 70° C. for 4 hours. The mixture was diluted with water and the aq. layer was extracted with EtOAc (3×). The organic layer was separated, dried over Na₂SO₄, filtered and the solvents concentrated in vacuo. The product was purified by column chromatography

Example A24

Preparation of Intermediate 25

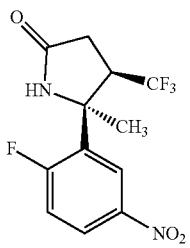

Nitric acid (fuming 90%, 0.2 mL) was added to a solution of intermediate 24 (500 mg, 1.91 mmol) in sulfuric acid (3.8 mL) and the mixture was stirred for 2 hours. The mixture was cooled down at 0° C., diluted with water and the aq. layer was extracted with EtOAc (3×). The organic layer was separated, dried over $Na_2SO_4$, filtered and the solvents concentrated in vacuo. The crude product was purified by column chromatography (silica gel; eluent: heptane/EtOAc 50/50 to 100/0) to afford intermediate 25 (520 mg, 89% yield, racemic mixture) as a solid (m.p. 230-232° C.).

Example A25

Preparation of Intermediate 26

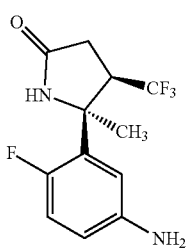

Palladium on carbon (10% wt/wt, 90 mg, 50 mol %) was added to a solution of intermediate 25 (520 mg, 1.70 mmol) in MeOH (34 mL). The mixture was stirred under hydrogen atmosphere (1 atm) overnight and then filtered through diatomaceous earth and the solvents concentrated in vacuo. The crude product was purified by column chromatography (silica gel; eluent: MeOH/EtOAc) to afford intermediate 26 (450 mg, 96% yield, racemic mixture) as a solid (m.p. 134-136° C.).

(silica gel; eluent: heptane/EtOAc 50/50 to 100/0) to afford intermediate 24 (322 mg, 73% yield, racemic mixture) as a solid (m.p. 179-181° C.).

Example A26

Preparation of Intermediate 27

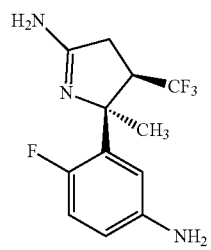 [SMILES: C[C@]1(c2cc(N)ccc2F)N=C(N)C[C@H]1C(F)(F)F]

$P_2S_5$ (290 mg, 1.3 mmol) was added to a solution of intermediate 26 (450 mg, 1.63 mmol) in THF (16 mL) and the mixture was heated at 50° C. for 2 hours. The resulting suspension was filtered and the filtrated was concentrated in in vacuo. The crude product was dissolved in 7M ammonia solution in MeOH (3.2 mL) and 32% aq. ammonia solution (8 mL) was added and the mixture was heated for 1 hour at 120° C. under microwave irradiation. The mixture was then diluted with water and extracted with DCM (33×). The organic layer was separated, dried over $Na_2SO_4$, filtered and the solvents concentrated in vacuo. The crude product was purified by column chromatography (silica gel; eluent: EtOAc/7M solution of ammonia in MeOH 90/10) to afford intermediate 27 (188 mg, 42% yield, racemic mixture) as a solid (m.p. 130-132° C.).

Alternatively, intermediate 27 can also be obtained starting from intermediate 24 by following a synthetic sequence similar to the one used for the synthesis of (in the order) intermediate 27, intermediate 25 and intermediate 26.

B. Preparation of the Final Compounds

Example B1

Preparation of compound 1: (4R,6S)-6-methyl-6-(3-pyrimidin-5-ylphenyl)-4-(trifluoromethyl)-3,4,5,6-tetrahydropyridin-2-amine and compound 2: (4S,6S)-6-methyl-6-(3-pyrimidin-5-ylphenyl)-4-(trifluoromethyl)-3,4,5,6-tetrahydropyridin-2-amine compound 1

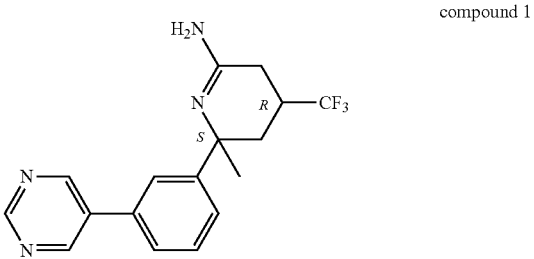

-continued compound 2

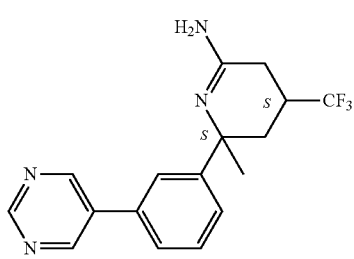

Intermediate 6 (0.284 g, 0.847 mmol), 5-pyrimidinylboronic acid (0.157 g, 1.271 mmol) and tetrakis(triphenylphosphine) palladium(0) (0.147 g, 0.127 mmol) were dissolved in a mixture of 1,4-dioxane (12 mL) and aq. NaHCO$_3$ (sat. sol., 1.5 mL). The resulting mixture was flushed with nitrogen and then heated at 80° C. for 2 hours. The r.m. was then diluted with water and extracted with DCM. The organic layer was separated, dried (Na$_2$SO$_4$), filtered and the solvents evaporated in vacuo. The crude product was purified by flash column chromatography (silica gel; eluent: DCM/7M solution of ammonia in MeOH 100/0 to 90/10). The desired fractions were collected and concentrated in vacuo. This residue was then purified by preparative SFC on Chiralpak® AD Daicel (20×250 mm; mobile phase: CO$_2$, MeOH with 0.2% iPrNH$_2$), yielding compound 1 (0.082 g, 29% yield) and another fraction, which was purified further by preparative HPLC (RP Vydac Denali C18-10 μM 200 g, 5 cm; mobile phase: 0.25% NH$_4$HCO$_3$ solution in water, MeCN), yielding compound 2 (5 mg, 2% yield).

Example B2

Preparation of compound 3: N-{3-[(2S,4R)-6-amino-2-methyl-4-(trifluoromethyl)-2,3,4,5-tetrahydropyridin-2-yl]phenyl}-5-methoxypyrazine-2-carboxamide and compound 4: N-{3-[(2S,4S)-6-amino-2-methyl-4-(trifluoromethyl)-2,3,4,5-tetrahydropyridin-2-yl]phenyl}-5-methoxypyrazine-2-carboxamide compound 3

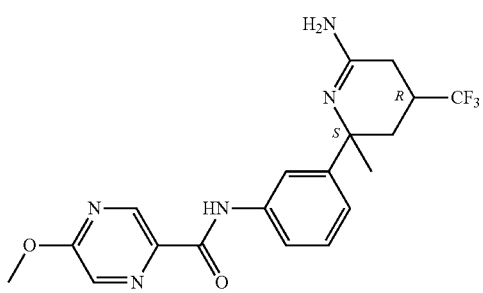

-continued compound 4

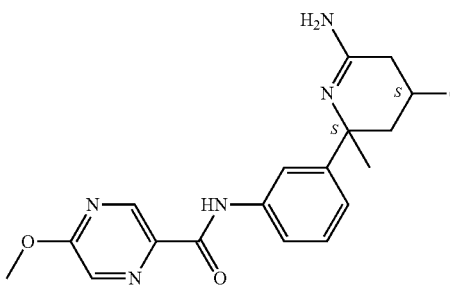

5-Methoxypyrazine-2-carboxylic acid (0.064 g, 0.417 mmol) was dissolved in MeOH (15 mL) and DMTMM (0.147 g, 0.5 mmol) was added. After stirring the mixture for 5 min, a solution of intermediate 7 (0.113 g, 0.417 mmol) in MeOH (5 mL) was added at 0° C., and the mixture was stirred for an additional 4 hours. The solvent was evaporated in vacuo. The crude product was purified by flash column chromatography (silica gel; eluent: DCM/7M solution of ammonia in MeOH 100/0 to 90/10). The desired fractions were collected and concentrated in vacuo. This residue was then purified by preparative SFC on Chiralpak® OD Daicel (20×250 mm; mobile phase: CO$_2$, MeOH with 0.2% iPrNH$_2$), yielding compound 3 (38 mg, 22% yield) and compound 4 (14 mg, 8% yield).

Example B3

Preparation of compound 5: N-[3-[(2S,4R)-6-amino-2-methyl-4-(trifluoromethyl)-4,5-dihydro-3H-pyridin-2-yl]phenyl]-5-chloro-3-fluoro-pyridine-2-carboxamide and compound 6: N-[3-[(2S,4S)-6-amino-2-methyl-4-(trifluoromethyl)-4,5-dihydro-3H-pyridin-2-yl]phenyl]-5-chloro-3-fluoro-pyridine-2-carboxamide compound 5

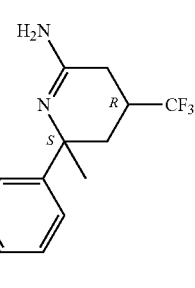

compound 6

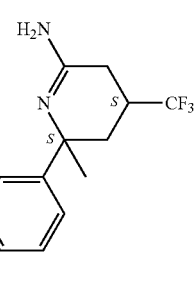

By following a synthetic procedure similar to the one used for the synthesis of compound 2 and compound 3, starting from 5-chloro-3-fluoropyridine-2-carboxylic acid a crude mixture was obtained, further purified by preparative SFC on Chiralcel® OD Daicel (20×250 mm; mobile phase: CO$_2$, MeOH with 0.2% iPrNH$_2$), to afford compound 5 (30 mg, 19% yield) and compound 6 (10 mg, 6% yield).

Example B4

Preparation of compound 7: N-[3-[(2S,4R)-6-amino-2-methyl-4-(trifluoromethyl)-4,5-dihydro-3H-pyridin-2-yl]phenyl]-5-cyano-pyridine-2-carboxamide and compound 8: N-[3-[(2S,4S)-6-amino-2-methyl-4-(trifluoromethyl)-4,5-dihydro-3H-pyridin-2-yl]phenyl]-5-cyano-pyridine-2-carboxamide compound 7

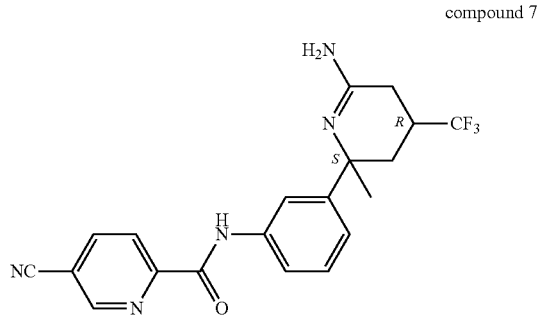

compound 8

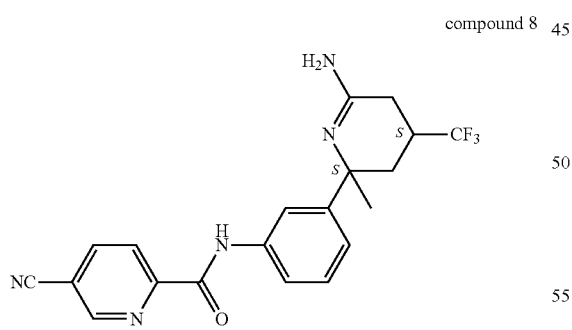

By following a synthetic procedure similar to the one used for the synthesis of compound 2 and compound 3, starting from 5-cyano-2-carboxylic acid a crude mixture was obtained, further purified first by preparative HPLC on RP Vydac Denali C18 (10 μM 200 g, 5 cm; mobile phase: 0.25% NH$_4$HCO$_3$ solution in water, MeCN) and then by preparative SFC on Chiralcel®OD Daicel (20×250 mm; mobile phase: CO$_2$, MeOH with 0.2% iPrNH$_2$), to afford compound 5 (30 mg, 19% yield) and compound 6 (10 mg, 6% yield).

Example B5

Preparation of compound 9: N-{3-[(2S,4R)-6-amino-2-methyl-4-(trifluoromethyl)-4,5-dihydro-3H-pyridin-2-yl]-4-fluoro-phenyl]-5-methoxy-pyrazine-2-carboxamide

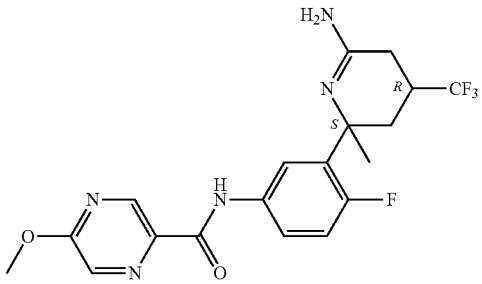

5-Methoxypyrazine-2-carboxylic acid (0.157 g, 1.02 mmol) was dissolved in MeOH (30 mL) and DMTMM (0.299 g, 1.02 mmol) was added. After stirring the mixture for 5 min, a solution of intermediate 14 (0.28 g, 0.968 mmol) in MeOH (10 mL) was added at 0° C. and the mixture was stirred overnight. The solvent was evaporated in vacuo. The crude product was purified by flash column chromatography (silica gel; eluent: DCM/7M ammonia in MeOH 100/0 to 92/8). The desired fractions were collected and concentrated in vacuo. Treatment with heptane afforded a white precipitate which was dried overnight (vacuum oven, 50° C.) yielding compound 9 (0.248 g, 60% yield).

Example B6

Preparation of compound 14: (±)-(2S*,3R*)-2-(4-fluoro-[1,1'-biphenyl]-3-yl)-2-methyl-3-(trifluoromethyl)-3,4-dihydro-2H-pyrrol-5-amine

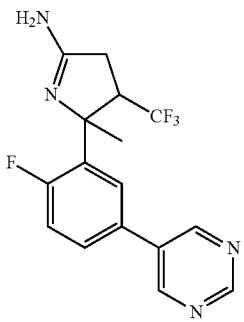 [SMILES: CC1(c2cc(-c3cncnc3)ccc2F)N=C(N)CC1C(F)(F)F]

Compound 14: C$_2$(RS);C$_3$(RS), Single Diastereoisomer (Cis)

Tetrakis(triphenylphosphine)palladium (16 mg, 0.014 mmol) and 5-pyrimidinylboronic acid (35 mg, 0.28 mmol) were added to a solution of rac-intermediate 19 (48 mg, 0.14 mmol) in a mixture of sat. aq. NaHCO$_3$ solution and dioxane (2.8:2.4 mL) and the mixture was heated at 80° C. for 2 hours. The mixture was diluted with water and extracted with DCM (3×). The organic layer was separated, dried over Na$_2$SO$_4$, filtered and the solvents concentrated in vacuo. The

Example B7

Preparation of compound 15: (±)-N-(3-((2S*,3R*)-5-amino-2-methyl-3-(trifluoromethyl)-3,4-dihydro-2H-pyrrol-2-yl)-4-fluorophenyl)-5-chloropicolinamide, compound 19: N-[3-[(2S,3R)-5-amino-2-methyl-3-(trifluoromethyl)-3,4-dihydropyrrol-2-yl]-4-fluoro-phenyl]-5-chloro-pyridine-2-carboxamide and compound 20: N-[3-[(2R,3S)-5-amino-2-methyl-3-(trifluoromethyl)-3,4-dihydropyrrol-2-yl]-4-fluoro-phenyl]-5-chloro-pyridine-2-carboxamide crude product was purified by column chromatography (silica gel; eluent: DCM/7M ammonia in MeOH 100/0 to 85/15) to afford compound 14 (33 mg, 69% yield, racemic mixture, cis).

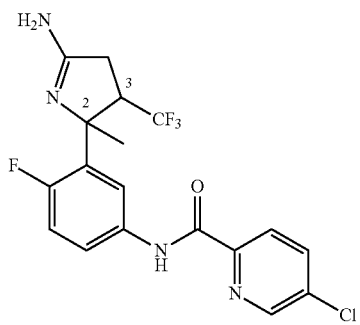

Compound 15: $C_2$(RS);$C_3$(RS), Single Diastereoisomer (Cis)

Compound 19: $C_2$(S);$C_3$(R), Single Diastereoisomer, Pure Enantiomer

Compound 20: $C_2$(R);$C_3$(S), Single Diastereoisomer, Pure Enantiomer

5-Chloropicolinic acid (29 mg, 0.18 mmol) was added to a solution of 4-(4,6-dimethoxy-1,3,5-triazin-2-yl)-4-methyl-morpholinium chloride (64 mg, 0.22 mmol) in MeOH (3.2 mL) at r.t. After 5 min stirring, a solution of rac-intermediate 27 in MeOH (3.2 mL) was added at 0° C. and the mixture was stirred for 16 h. The solvent was evaporated in vacuo and the crude product was purified by column chromatography (silica gel; eluent: DCM/7M ammonia in MeOH 100/10 to 95/5). The desired fractions were collected and concentrated in vacuo to afford compound 15 (28 mg, 37% yield, racemic mixture) as a white solid further purified by chiral SFC on Chiralcel® OD-H (20×250 mm; mobile phase: 60% $CO_2$, 40% EtOH with 0.3% iPrNH$_2$), to afford compound 19 (13 mg, 9% yield) and compound 20 (14 mg, 9% yield).

Example B8

Preparation of compound 16: (±)-N-[3-1[(2S*,3R*)-5-amino-2-methyl-3-(trifluoromethyl)-3,4-dihydropyrrol-2-yl]-4-fluoro-phenyl]-2-methyl-oxazole-4-carboxamide, compound 35: N-[3-[(2R,3S)-5-amino-2-methyl-3-(trifluoromethyl)-3,4-dihydropyrrol-2-yl]-4-fluoro-phenyl]-2-methyl-oxazole-4-carboxamide and compound 36: N-[3-[(2S,3R)-5-amino-2-methyl-3-(trifluoromethyl)-3,4-dihydropyrrol-2-yl]-4-fluoro-phenyl]-2-methyl-oxazole-4-carboxamide

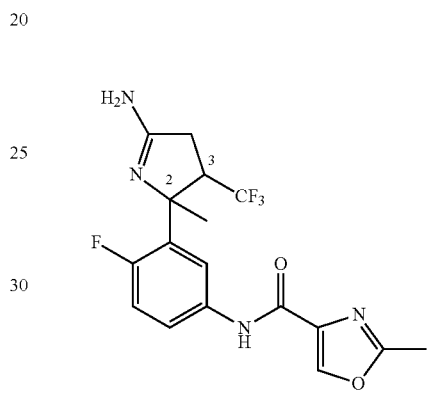

Compound 16: $C_2$(RS);$C_3$(RS), Single Diastereoisomer (Cis)

Compound 35: $C_2$(R);$C_3$(S), Single Diastereoisomer, Pure Enantiomer

Compound 36: $C_2$(S);$C_3$(R), Single Diastereoisomer, Pure Enantiomer

By following a synthetic procedure similar to the one used for the synthesis of compound 15, starting from 2-methyl-oxazole-4-carboxylic acid compound 16 (70 mg, 28% yield) was obtained after purification by preparative HPLC on C18 Xbridge (30×100 mm, 5 µm; mobile phase: gradient from 74% 10 mM NH$_4$CO$_3$H pH 9 solution in water, 26% MeCN to 58% 10 mM NH$_4$CO$_3$H pH 9 solution in water, 42% MeCN). Subsequent separation by chiral SFC on Chiralpak® AD-H Daicel (20×250 mm, 5 km; mobile phase: 80% $CO_2$, 20% iPrOH with 0.3% iPrNH$_2$) afforded compound 35 (24 mg, 10% yield) and compound 36 (29 mg, 12% yield).

Example B9

Preparation of compound 17: (±)-N-[3-[(2S*,3R*)-5-amino-2-methyl-3-(trifluoromethyl)-3,4-dihydro-pyrrol-2-yl]-4-fluoro-phenyl]-5-methoxy-pyrazine-2-carboxamide, compound 27: N-[3-[(2R,3S)-5-amino-2-methyl-3-(trifluoromethyl)-3,4-dihydropyrrol-2-yl]-4-fluoro-phenyl]-5-methoxy-pyrazine-2-carboxamide and compound 34: N-[3-[(2S,3R)-5-amino-2-methyl-3-(trifluoromethyl)-3,4-dihydropyrrol-2-yl]-4-fluoro-phenyl]-5-methoxy-pyrazine-2-carboxamide

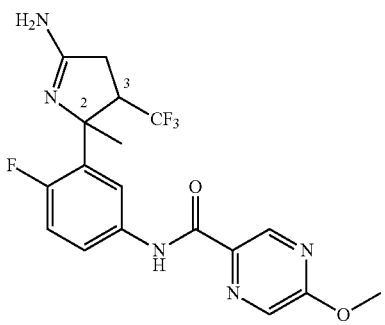 [SMILES: COc1cnc(C(=O)Nc2ccc(F)c(C3(C)N=C(N)CC3C(F)(F)F)c2)cn1]

Compound 17: $C_2(RS);C_3(RS)$, Single Diastereoisomer (Cis)

Compound 27: $C_2(R);C_3(S)$, Single Diastereoisomer, Pure Enantiomer

Compound 34: $C_2(S);C_3(R)$, Single Diastereoisomer, Pure Enantiomer

By following a synthetic procedure similar to the one used for the synthesis of compound 15, starting from 5-methoxy-pyrazine-2-carboxylic acid compound 17 (96 mg, 36% yield) was obtained, further purified by chiral SFC on Chiralcel® OD-H Daicel (20×250 mm, 5 m; mobile phase: 60% $CO_2$, 40% EtOH with 0.3% $iPrNH_2$), to afford compound 27 (30 mg, 11% yield) and compound 34 (34 mg, 13% yield).

Example B10

Preparation of compound 18: (+)-N-[3-[(2S*,3R*)-5-amino-2-methyl-3-(trifluoromethyl)-3,4-dihydro-pyrrol-2-yl]-4-fluoro-phenyl]-5-cyano-pyridine-2-carboxamide, compound 25: N-[3-[(2R,3S)-5-amino-2-methyl-3-(trifluoromethyl)-3,4-dihydropyrrol-2-yl]-4-fluoro-phenyl]-5-cyano-pyridine-2-carboxamide and compound 26: N-[3-[(2S,3R)-5-amino-2-methyl-3-(trifluoromethyl)-3,4-dihydropyrrol-2-yl]-4-fluoro-phenyl]-5-cyano-pyridine-2-carboxamide

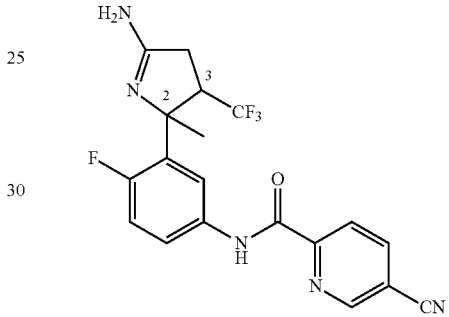

Compound 18: $C_2(RS);C_3(RS)$, Single Diastereoisomer (Cis)

Compound 25: $C_2(R);C_3(S)$, Single Diastereoisomer, Pure Enantiomer

Compound 26: $C_2(S);C_3(R)$, Single Diastereoisomer, Pure Enantiomer

By following a synthetic procedure similar to the one used for the synthesis of compound 15, starting from 5-cyano-2-carboxylic acid compound 18 (80 mg, 30% yield) was obtained after purification by preparative HPLC on C18 Xbridge (30×100 mm, 5 μm; mobile phase; gradient from 74% 10 mM $NH_4CO_3H$ pH 9 solution in water, 26% MeCN to 58% 10 mM $NH_4CO_3H$ pH 9 solution in water, 42% MeCN). Subsequent separation by chiral SFC on Chiralcel® OD-H (20×250 mm, 5 m; mobile phase: 60% $CO_2$, 40% EtOH with 0.3% $iPrNH_2$), afforded compound 25 (30 mg, 11% yield) and compound 26 (28 mg, 11% yield).

Example B11

Preparation of compound 21: (+)-N-[3-[(2S*,3R*)-5-amino-2-methyl-3-(trifluoromethyl)-3,4-dihydro-pyrrol-2-yl]-4-fluoro-phenyl]-3-methoxy-pyridin-2-amine, compound 37: N-[3-[(2S,3R)-5-amino-2-methyl-3-(trifluoromethyl)-3,4-dihydropyrrol-2-yl]-4-fluoro-phenyl]-3-methoxy-pyridin-2-amine and compound 28: N-[3-[(2R,3S)-5-amino-2-methyl-3-(trifluoromethyl)-3,4-dihydropyrrol-2-yl]-4-fluoro-phenyl]-3-methoxy-pyridin-2-amine

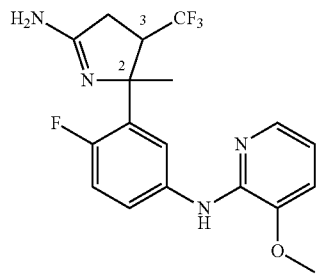 [SMILES: COc1cccnc1Nc1ccc(F)c(C2(C)N=C(N)CC2C(F)(F)F)c1]

Compound 21: $C_2(RS);C_3(RS)$, Single Diastereoisomer (Cis)

Compound 37: $C_2(S);C_3(R)$, Single Diastereoisomer, Pure Enantiomer

Compound 42: $C_2(R);C_3(S)$, Single Diastereoisomer, Pure Enantiomer

Intermediate 27 (200 mg, 0.727 mmol) was dissolved in iPrOH (8.8 mL). 2-Bromo-3-methoxypyridine (273 mg, 1.45 mmol) was then added, followed by $H_2SO_4$ (0.19 mL, 3.6 mmol). The reaction mixture was stirred at 80° C. for 7 days, then cooled to r.t. and DCM and $NaHCO_3$ sat. solution were added. The product was extracted and the organic layer was dried over $Na_2SO_4$, filtered and concentrated in vacuo to yield a yellow oil, purified by column chromatography (silica gel; eluent: DCM/7M solution of ammonia in MeOH 100/0 to 92/8). The desired fractions were collected and concentrated in vacuo to yield a yellow solid, further purified by RP HPLC on C18 XBridge (30×100 mm 5 km; mobile phase: gradient from 67% 10 mM $NH_4CO_3H$ pH 9 solution in water, 33% MeCN to 50% 10 mM $NH_4CO_3H$ pH 9 solution in water, 50% MeCN), yielding compound 21 (135 mg, 49%) as a white solid. Further separation by chiral SFC on Chiralpak® AD-H (5 μm 250×20 mm; mobile phase: 80% $CO_2$, 20% EtOH with 0.3% $iPrNH_2$) yielded compound 37 (49 mg, 18%) and compound 28 (51 mg, 18%).

Example B12

Preparation of compound 22: (±)-2-[3-[(2S*,3R*)-5-amino-2-methyl-3-(trifluoromethyl)-3,4-dihydro-pyrrol-2-1]-4-fluoro-anilino]pyridine-3-carbonitrile, compound 38: 2-[3-[(2S,3R)-5-amino-2-methyl-3-(trifluoromethyl)-3,4-dihydropyrrol-2-yl]-4-fluoro-anilino]pyridine-3-carbonitrile and compound 39: 2-[3-[(2R,3S)-5-amino-2-methyl-3-(trifluoromethyl)-3,4-dihydropyrrol-2-yl]-4-fluoro-anilino]pyridine-3-carbonitrile

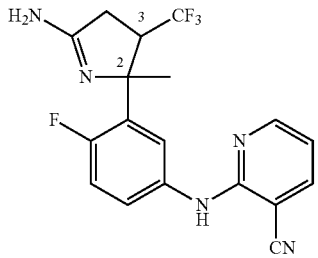 [SMILES: CC1(c2cc(Nc3ncccc3C#N)ccc2F)N=C(N)CC1C(F)(F)F]

Compound 22: $C_2(RS);C_3(RS)$, Single Diastereoisomer (Cis)

Compound 38: $C_2(S);C_3(R)$, Single Diastereoisomer, Pure Enantiomer

Compound 39: $C_2(R);C_3(S)$, Single Diastereoisomer, Pure Enantiomer

By following a synthetic procedure similar to the one used for the synthesis of compound 21, starting from 2-chloronicotinonitrile compound 22 (27 mg, 10% yield) was obtained after purification by RP HPLC on C18 XBridge (30×100 mm 5 μm; mobile phase: gradient from 67% 10 mM $NH_4CO_3H$ pH 9 solution in water, 33% MeCN to 50% 10 mM $NH_4CO_3H$ pH 9 solution in water, 50% MeCN). Further separation by chiral SFC on Chiralcel® OD-H (5 μm 250×20 mm; mobile phase: 70% $CO_2$, 30% EtOH with 0.3% $iPrNH_2$) yielded two fractions, each of them further purified by RP HPLC on C18 XBridge (30×150 mm; mobile phase: gradient from 90% $NH_4CO_3H$ 0.5% solution in water, 10% MeCN to 0% $NH_4CO_3H$ 0.5% solution in water, 100% MeCN). Compound 38 (7 mg, 3% yield) and compound 39 (8 mg, 3% yield) were obtained.

Example B13

Preparation of compound 23: (±)-N-[3-[(2S*,3R*)-5-amino-2-methyl-3-(trifluoromethyl)-3,4-dihydro-pyrrol-2-yl]-4-fluoro-phenyl]-5-(2-methoxyethoxy)pyrazine-2-carboxamide, compound 29: N-[3-[(2R,3S)-5-amino-2-methyl-3-(trifluoromethyl)-3,4-dihydropyrrol-2-yl]-4-fluoro-phenyl]-5-(2-methoxyethoxy)pyrazine-2-carboxamide and compound 30: N-[3-[(2S,3R)-5-amino-2-methyl-3-(trifluoromethyl)-3,4-dihydropyrrol-2-yl]-4-fluoro-phenyl]-5-(2-methoxyethoxy)pyrazine-2-carboxamide

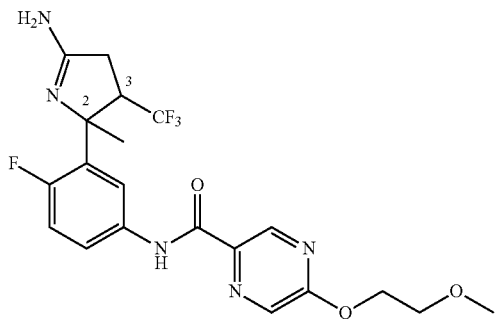 [SMILES: COCCOc1cnc(C(=O)Nc2ccc(F)c(C3(C)N=C(N)CC3C(F)(F)F)c2)cn1]

Compound 23: $C_2(RS);C_3(RS)$, Single Diastereoisomer (Cis)

Compound 29: $C_2(R);C_3(S)$, Single Diastereoisomer, Pure Enantiomer

Compound 30: $C_2(S);C_3(R)$, Single Diastereoisomer, Pure Enantiomer

By following a synthetic procedure similar to the one used for the synthesis of compound 15, starting from 5-(2-methoxyethoxy)-2-pyrazinecarboxylic acid compound 23 (150 mg, 18% yield) was obtained after purification by RP HPLC on C18 XBridge (30×100 mm 5 min; mobile phase: gradient from 74% 10 mM $NH_4CO_3H$ pH 9 solution in water, 26% MeCN to 58% 10 mM $NH_4CO_3H$ pH 9 solution in water, 42% MeCN). Further separation first by achiral SFC on CYANO (6 μm 150×21.2 mm; mobile phase: 80% $CO_2$, 20% iPrOH with 0.3% $iPrNH_2$) and then by chiral SFC on Chiralcel® OD-H (5 μm 250×20 mm; mobile phase: 70% $CO_2$, 30% EtOH with 0.3% $iPrNH_2$) yielded compound 29 (27 mg, 3% yield) and compound 30 (29 mg, 4% yield).

Example B14

Preparation of compound 24: (±)-N-[3-[(2S*,3R*)-5-amino-2-methyl-3-(trifluoromethyl)-3,4-dihydro-pyrrol-2-yl]-4-fluoro-phenyl]-5-(2,2,2-trifluoroethoxy)pyrazine-2-carboxamide, compound 31: N-[3-[(2R,3S)-5-amino-2-methyl-3-(trifluoromethyl)-3,4-dihydropyrrol-2-yl]-4-fluoro-phenyl]-5-(2,2,2-trifluoroethoxy)pyrazine-2-carboxamide and compound 32: N-[3-[(2S,3R)-5-amino-2-methyl-3-(trifluoromethyl)-3,4-dihydropyrrol-2-yl]-4-fluoro-phenyl]-5-(2,2,2-trifluoroethoxy)pyrazine-2-carboxamide

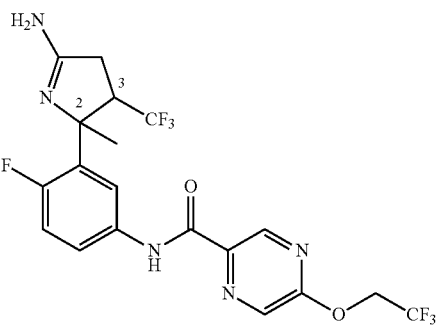

Compound 24: $C_2(RS);C_3(RS)$, Single Diastereoisomer (Cis)

Compound 31: $C_2(R);C_3(S)$, Single Diastereoisomer, Pure Enantiomer

Compound 32: $C_2(S);C_3(R)$, Single Diastereoisomer, Pure Enantiomer

By following a synthetic procedure similar to the one used for the synthesis of compound 15, starting from 5-(2,2,2-trifluoroethoxy)pyrazine-2-carboxylic acid compound 24 (27 mg, 18% yield) was obtained after purification by RP HPLC on C18 XBridge (30×100 mm 5 km; mobile phase: gradient from 67% 10 mM $NH_4CO_3H$ pH 9 solution in water, 33% MeCN to 50% 10 mM $NH_4CO_3H$ pH 9 solution in water, 50% MeCN). Further separation by chiral SFC on Chiralcel® OD-H (5 μm 250×20 mm; mobile phase: 70% $CO_2$, 30% EtOH with 0.3% $iPrNH_2$) yielded compound 31 (9 mg, 6% yield) and compound 32 (10 mg, 6% yield).

Example B15

Preparation of compound 40: (±)-N-[3-[(2S*,3R*)-5-amino-2-methyl-3-(trifluoromethyl)-3,4-dihydro-pyrrol-2-yl]-4-fluoro-phenyl]-5-bromo-pyridine-2-carboxamide, compound 33: N-[3-[(2R,3S)-5-amino-2-methyl-3-(trifluoromethyl)-3,4-dihydropyrrol-2-yl]-4-fluoro-phenyl]-5-bromo-pyridine-2-carboxamide and compound 41: N-[3-[(2S,3R)-5-amino-2-methyl-3-(trifluoromethyl)-3,4-dihydropyrrol-2-yl]-4-fluoro-phenyl]-5-bromo-pyridine-2-carboxamide

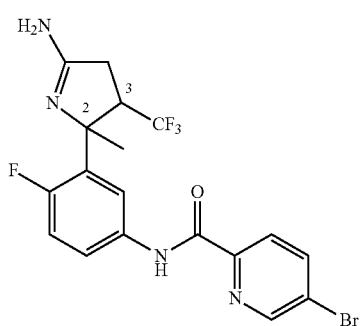 [SMILES: CC1(c2cc(NC(=O)c3ccc(Br)cn3)ccc2F)N=C(N)CC1C(F)(F)F]

Compound 40: $C_2(RS);C_3(RS)$, Single Diastereoisomer (Cis)

Compound 33: $C_2(R);C_3(S)$, Single Diastereoisomer, Pure Enantiomer

Compound 41: $C_2(S);C_3(R)$, Single Diastereoisomer, Pure Enantiomer

By following a synthetic procedure similar to the one used for the synthesis of compound 15, starting from 5-(2,2,2-trifluoroethoxy)pyrazine-2-carboxylic acid compound 40 (140 mg, 21% yield) was obtained after purification by RP HPLC on C18 XBridge (30×100 mm 5 Gm; mobile phase: gradient from 67% 10 mM $NH_4CO_3H$ pH 9 solution in water, 33% MeCN to 50% 10 mM $NH_4CO_3H$ pH 9 solution in water, 50% MeCN). Further separation by chiral SFC on Chiralcel® OD-H (5 μm 250×20 mm; mobile phase: 60% $CO_2$, 40% EtOH with 0.3% $iPrNH_2$) yielded compound 33 (54 mg, 8% yield) and compound 41 (57 mg, 8% yield).

Compounds 1 to 13 in table 1 and compounds 14 to 41 in table 2 list the compounds that were prepared by analogy to one of the above Examples. In case no salt form is indicated, the compound was obtained as a free base. 'Ex. No.' refers to the Example number according to which protocol the compound was synthesized. 'Co. No.' means compound number.

TABLE 1

| Co. No. | Ex. No. | R² | —L—Ar | stereochemistry |
|---|---|---|---|---|
| 1 | B1 | H | pyrimidinyl | $C_4(R);C_6(S)$ Single diastereoisomer Pure enantiomer |
| 2 | B1 | H | pyrimidinyl | $C_4(S);C_6(S)$ Single diastereoisomer Pure enantiomer |
| 3 | B2 | H | -NHC(O)-pyrazine-OMe | $C_2(S);C_4(R)$ Single diastereoisomer Pure enantiomer |
| 4 | B2 | H | -NHC(O)-pyrazine-OMe | $C_2(S);C_4(S)$ Single diastereoisomer Pure enantiomer |
| 5 | B3 | H | -NHC(O)-pyridine(F)(Cl) | $C_2(S);C_4(R)$ Single diastereoisomer Pure enantiomer |
| 6 | B3 | H | -NHC(O)-pyridine(F)(Cl) | $C_2(S);C_4(S)$ Single diastereoisomer Pure enantiomer |
| 7 | B4 | H | -NHC(O)-pyridine-CN | $C_2(S);C_4(R)$ Single diastereoisomer Pure enantiomer |
| 8 | B4 | H | -NHC(O)-pyridine-CN | $C_2(S);C_4(S)$ Single diastereoisomer Pure enantiomer |

TABLE 1-continued

[Structure: 2-amino-6-methyl-4-(trifluoromethyl)-6-(2-R2-5-(L-Ar)phenyl)-tetrahydropyridine]

| Co. No. | Ex. No. | R² | —L—Ar | stereochemistry |
|---|---|---|---|---|
| 9 | B5 | F | *N*-linked amide to 5-methoxypyrazine-2-carboxamide | C₂(S);C₄(R) Single diastereoisomer Pure enantiomer |
| 10 | B5 | F | *N*-linked amide to 5-cyanopyridine-2-carboxamide | C₂(S);C₄(R) Single diastereoisomer Pure enantiomer |
| 11 | B5 | F | *N*-linked amide to 5-chloropyridine-2-carboxamide | C₂(S);C₄(R) Single diastereoisomer Pure enantiomer |
| 12 | B5 | F | *N*-linked amide to 5-fluoropyridine-2-carboxamide | C₂(S);C₄(R) Single diastereoisomer Pure enantiomer |
| 13 | B5 | F | *N*-linked amide to 1-(difluoromethyl)-1H-pyrazole-3-carboxamide | C₂(S);C₄(R) Single diastereoisomer Pure enantiomer |

TABLE 2

[Structure: 2-amino-5-methyl-3-(trifluoromethyl)-5-(2-R2-5-(L-Ar)phenyl)-dihydropyrrole]

| Co. No. | Ex. No. | R² | —L—Ar | stereochemistry |
|---|---|---|---|---|
| 14 | B6 | F | pyrimidin-5-yl | C₂(RS);C₃(RS) Single diastereoisomer (cis) |
| 15 | B7 | F | *N*-linked amide to 5-chloropyridine-2-carboxamide | C₂(RS);C₃(RS) Single diastereoisomer (cis) |
| 16 | B8 | F | *N*-linked amide to 2-methyloxazole-4-carboxamide | C₂(RS);C₃(RS) Single diastereoisomer (cis) |

TABLE 2-continued

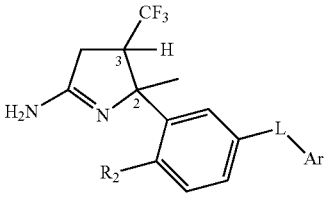

| Co. No. | Ex. No. | R² | —L—Ar | stereochemistry |
|---|---|---|---|---|
| 17 | B9 | F | 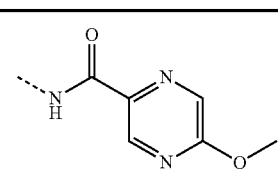 | C₂(RS);C₃(RS) Single diastereoisomer (cis) |
| 18 | B10 | F | 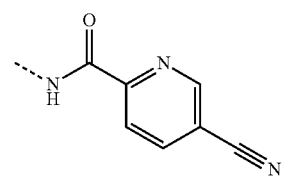 | C₂(RS);C₃(RS) Single diastereoisomer (cis) |
| 19 | B7 | F | 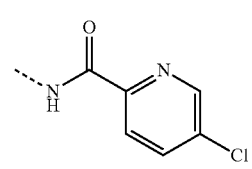 | C₂(S);C₃(R) Single diastereoisomer (cis) |
| 20 | B7 | F | 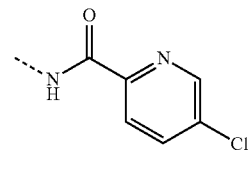 | C₂(R);C₃(S) Single diastereoisomer Pure enantiomer |
| 21 | B11 | F | 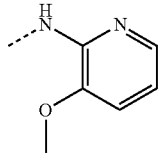 | C₂(RS);C₃(RS) Single diastereoisomer (cis) |
| 22 | B12 | F | 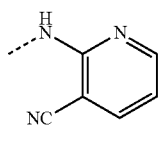 | C₂(RS);C₃(RS) Single diastereoisomer (cis) |
| 23 | B13 | F | 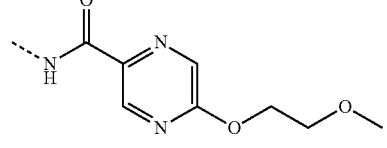 | C₂(RS);C₃(RS) Single diastereoisomer (cis/trans: 92/8) |
| 24 | B14 | F | 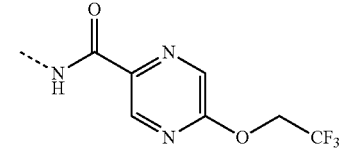 | C₂(S);C₃(R) Single diastereoisomer Pure enantiomer |

TABLE 2-continued

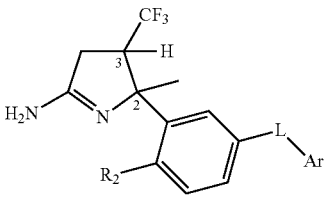

| Co. No. | Ex. No. | R² | —L—Ar | stereochemistry |
|---|---|---|---|---|
| 25 | B10 | F | 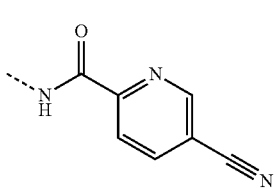 | C₂(R);C₃(S) Single diastereoisomer Pure enantiomer |
| 26 | B10 | F | 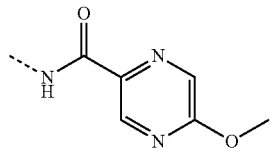 | C₂(S);C₃(R) Single diastereoisomer Pure enantiomer |
| 27 | B9 | F | 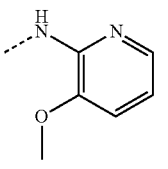 | C₂(R);C₃(S) Single diastereoisomer Pure enantiomer |
| 28 | B11 | F | 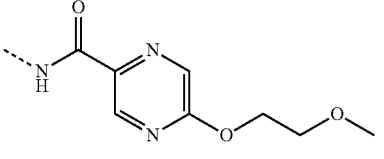 | C₂(R);C₃(S) Single diastereoisomer Pure enantiomer |
| 29 | B13 | F | 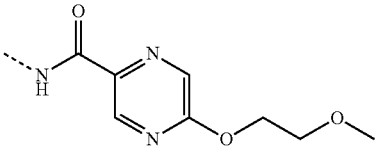 | C₂(R);C₃(S) Single diastereoisomer Pure enantiomer |
| 30 | B13 | F | 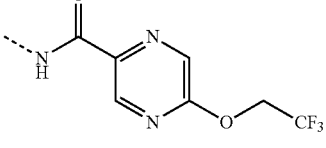 | C₂(S);C₃(R) Single diastereoisomer Pure enantiomer |
| 31 | B14 | F | 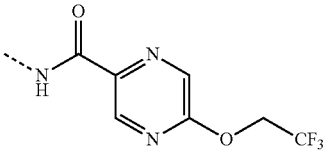 | C₂(R);C₃(S) Single diastereoisomer Pure enantiomer |
| 32 | B14 | F | | C₂(S);C₃(R) Single diastereoisomer Pure enantiomer |

TABLE 2-continued

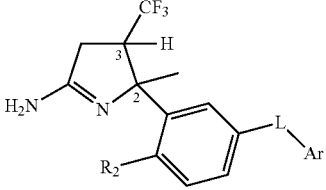

| Co. No. | Ex. No. | R² | —L—Ar | stereochemistry |
|---|---|---|---|---|
| 33 | B15 | F | 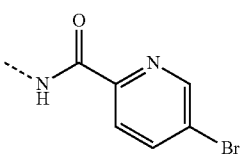 | C₂(R);C₃(S) Single diastereoisomer Pure enantiomer |
| 34 | B9 | F | 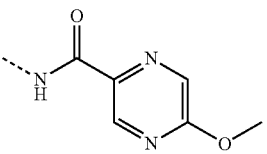 | C₂(S);C₃(R) Single diastereoisomer Pure enantiomer |
| 35 | B8 | F | 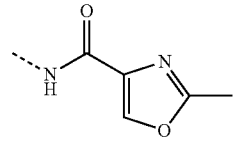 | C₂(R);C₃(S) Single diastereoisomer Pure enantiomer |
| 36 | B8 | F | 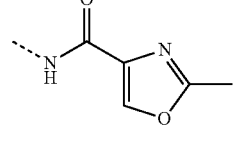 | C₂(S);C₃(R) Single diastereoisomer Pure enantiomer |
| 37 | B11 | F | 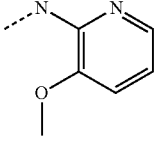 | C₂(S);C₃(R) Single diastereoisomer Pure enantiomer |
| 38 | B12 | F | 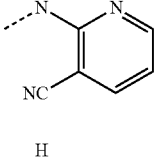 | C₂(S);C₃(R) Single diastereoisomer Pure enantiomer |
| 39 | B12 | F | 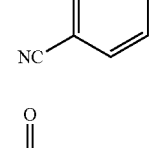 | C₂(R);C₃(S) Single diastereoisomer Pure enantiomer |
| 40 | B15 | F | 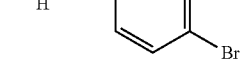 | C₂(RS);C₃(RS) Single diastereoisomer (cis) |

TABLE 2-continued

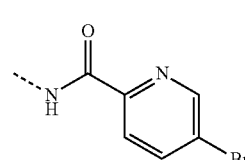

| Co. No. | Ex. No. | R² | —L—Ar | stereochemistry |
|---|---|---|---|---|
| 41 | B11 | F | (pyridine-2-carboxamide with 5-Br) | C₂(S);C₃(R)<br>Single diastereoisomer<br>Pure enantiomer |

C. Analytical Part

LCMS (Liquid Chromatography/Mass Spectrometry)
LCMS General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times ($R_t$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, [M+CH₃COO]⁻, etc. . . . ). For molecules with multiple isotopic patterns (e.g. Br, Cl), the reported value is the one obtained for the lowest isotope mass. All results were obtained with experimental uncertainties that are commonly associated with the method used.

Hereinafter, "UPLC" Ultra Performance Liquid Chromatography, "DAD" Diode Array Detector, "SQD" Single Quadrupole Detector, "QTOF" Quadrupole-Time of Flight, "RT" room temperature, "BEH" bridged ethylsiloxane/silica hybrid, "CSH" charged surface hybrid.

TABLE 3

LCMS Method codes (Flow expressed in mL/min; column temperature (T) in ° C.; Run time in minutes)

| Method code | Instrument | Column | Mobile phase | Gradient | Flow / Col T | Run time |
|---|---|---|---|---|---|---|
| 1 | Waters: Acquity® UPLC® - DAD/SQD | Waters: BEH C18 (1.7 µm, 2.1 * 50 mm) | A: 10 mM CH₃COONH₄ in 95% H₂O + 5% MeCN B: MeCN | From 95% A to 5% A in 1.3 min, held for 7 min. | 0.8 / 55 | 2 |
| 2 | Waters: Acquity® UPLC® - DAD/SQD | Agilent: Eclipse Plus C18 RRHD (1.8 µm, 2.1 × 50 mm) | A: 95% CH₃COONH₄ 6.5 mM + 5% MeCN, B: MeCN | From 95% A to 5% A in 4.6 min, held for 0.4 min | 1 / 50 | 5 |
| 3 | Waters: Acquity® IClass UPLC® - DAD/ Xevo G2-S QTOF | Waters: CSH™ C18 (1.7 µm, 2.1 × 50 mm) | A: 95% CH₃COONH₄ 6.5 mM + 5% MeCN B: MeCN | From 95% A to 5% A in 4.6 min, held for 0.4 min | 1 / 50 | 5 |
| 4 | Waters: Acquity UPLC® - DAD/ Quattro Micro™ | Waters: BEH C18 (1.7 µm, 2.1 × 100 mm) | A: 95% CH₃CO₀NH₄ 7 mM/5% MeCN B: MeCN | 84.2% A for 0.49 min, to 10.5% A in 2.18 min, held for 1.94 min, back to 84.2% A in 0.73 min, held for 0.73 min. | 0.343 / 40 | 6.2 |

TABLE 3-continued

LCMS Method codes (Flow expressed in mL/min; column temperature (T) in ° C.; Run time in minutes)

| Method code | Instrument | Column | Mobile phase | Gradient | Flow / ColT | Run time |
|---|---|---|---|---|---|---|
| 5 | Waters: Acquity ® IClass UPLC ® - DAD/SQD | Waters: CSH ™ C18 (1.7 μm, 2.1 × 50 mm) | A: 95% $CH_3COONH_4$ 6.5 mM + 5% MeCN  B: MeCN | From 95% A to 5% A in 4.6 min, held for 0.4 min | 1 / 50 | 5 |

Melting Points

Values are either peak values or melt ranges, and are obtained with experimental uncertainties that are commonly associated with this analytical method.

TABLE 4

Analytical data - melting point (m.p.) and LC/MS: $R_t$ means retention time (in minutes), $[M + H]^+$ means the protonated mass of the compound, $[M - H]^-$ means the deprotonated mass of the compound, method refers to the method used for (LC)MS. For some compounds, the exact mass was determined.

| Co. Nr. | $R_t$ | $[M + H]^+$ | $[M - H]^-$ | Method | m.p. (° C.) |
|---|---|---|---|---|---|
| 1 | 0.61 | 335 | | 1 | b.r. |
| 2 | 0.66 | 335 | | 1 | n.d. |
| 3 | 0.8 | 408 | | 1 | 171.93 |
| 4 | 0.82 | 408 | | 1 | 138.66 |
| 5 | 0.85 | 429 | | 1 | b.r. |
| 6 | 0.87 | 429 | | 1 | b.r. |
| 7 | 0.76 | 402 | | 1 | n.d. |
| 8 | 0.81 | 402 | | 1 | n.d. |
| 9 | 0.88 | 426 | | 1 | b.r. |
| 10 | 0.86 | 420 | | 1 | 205.8 |
| 11 | 0.95 | 429 | | 1 | n.d. |
| 12 | 0.89 | 413 | | 1 | 199.22 |
| 13 | 0.85 | 434 | | 1 | 139.83 |
| 14 | 1.04 | 339 | | 2 | n.d. |
| 15 | 1.78 | 415.0946 (−0.3 mDa) | | 3 | 240.62 |
| 16 | 1.26 | 385.1284 (−0.3 mDa) | | 3 | 207.05 |
| 17 | 1.58 | 412.1394 (−0.2 mDa) | | 3 | n.d. |
| 18 | 1.51 | 406.1288 (−0.3 mDa) | | 3 | 253.81 |
| 19 | 2.49 | 415 | 413 | 4 | n.d. |
| 20 | 2.50 | 415 | 413 | 4 | n.d. |
| 21 | 1.80 | 383.1498 (+0.3 mDa) | | 3 | 184.20 |
| 22 | 1.54 | — | 376.1187 (+0.1 mDa) | 3 | n.d. |
| 23 | 1.51 | 456 | 454 | 5 | 165.48 |
| 24 | 2.05 | 480.1270 (+0.0 mDa) | | 3 | 213.21 |
| 25 | 2.25 | 406 | 404 | 4 | n.d. |
| 26 | 2.25 | 406 | 404 | 4 | n.d. |
| 27 | 2.27 | 412 | 410 | 4 | n.d. |
| 28 | 2.40 | 383 | 381 | 4 | n.d. |
| 29 | 2.28 | 456 | 454 | 4 | n.d. |
| 30 | 2.27 | 456 | 454 | 4 | n.d. |
| 31 | 2.60 | 480 | 478 | 4 | n.d. |
| 32 | 2.62 | 480 | 478 | 4 | n.d. |
| 33 | 2.48 | 459 | 457 | 4 | n.d. |
| 34 | 2.27 | 412 | 410 | 4 | n.d. |
| 35 | 2.07 | 385 | 383 | 4 | n.d. |
| 36 | 2.06 | 385 | 383 | 4 | n.d. |
| 37 | 2.40 | 383 | 381 | 4 | n.d. |
| 38 | 2.29 | 378 | 376 | 4 | n.d. |
| 39 | 2.29 | 378 | 376 | 4 | n.d. |
| 40 | 1.90 | 459.0467 (+2.4 mDa) | | 3 | 243.40 |
| 41 | 2.48 | 459 | 457 | 4 | n.d. | n.d. means not determined,
b.r. means broad range

Optical Rotations:

Optical rotations were measured on a Perkin-Elmer 341 polarimeter with a sodium lamp and reported as follows: $[\alpha]°$ (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 5

Analytical data - Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 1 | −35.82 | 589 | 0.268 | DMF | 20 |
| 3 | −24.77 | 589 | 0.222 | DMF | 20 |
| 9 | +99.2 | 589 | 0.375 | DMF | 20 |
| 10 | +121 | 589 | 0.3 | DMF | 20 |
| 11 | +70 | 589 | 0.25 | DMF | 20 |
| 12 | +103.6 | 589 | 0.25 | DMF | 20 |
| 13 | +80.8 | 589 | 0.25 | DMF | 20 |
| 19 | +29.9 | 589 | 0.5 | DMF | 20 |
| 20 | −30.4 | 589 | 0.5 | DMF | 20 |
| 25 | +36.1 | 589 | 0.5 | DMF | 20 |
| 26 | −44.7 | 589 | 0.5 | DMF | 20 |
| 27 | +40.9 | 589 | 0.5 | DMF | 20 |
| 28 | +35.6 | 589 | 0.5 | DMF | 20 |
| 29 | +39.8 | 589 | 0.5 | DMF | 20 |
| 30 | −35.0 | 589 | 0.8 | DMF | 20 |
| 31 | +20.2 | 589 | 0.5 | DMF | 20 |
| 32 | −17.0 | 589 | 0.5 | DMF | 20 |
| 33 | +38.7 | 589 | 0.5 | DMF | 20 |
| 34 | −34.7 | 589 | 0.5 | DMF | 20 |
| 35 | −23.5 | 589 | 0.5 | DMF | 20 |
| 36 | +18.5 | 589 | 0.5 | DMF | 20 |
| 37 | −46.3 | 589 | 0.5 | DMF | 20 |

TABLE 5-continued

Analytical data - Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 38 | +1.5 | 589 | 0.7 | MeOH | 20 |
| 39 | −1.0 | 589 | 0.7 | MeOH | 20 |
| 40 | n.d. | 589 | 0.5 | DMF | 20 |
| 41 | −30.0 | 589 | 0.5 | DMF | 20 |

SFCMS-Methods:
General Procedure a for SFC-MS Methods

The SFC measurement was performed using Analytical Supercritical fluid chromatography (SFC) system composed by a binary pump for delivering carbon dioxide (CO2) and modifier, an autosampler, a columns oven with switching valve for column heating from room temperature to 80° C., a diode array detector equipped with a high-pressure flow cell standing up to 400 bars. Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Method 1:
In addition to the general procedure A: The chiral separation in SFC was carried out on a CHIRALCEL OD-H column (4.6×250 mm) at 030° C. with a flow rate of 3.0 ml/min. The mobile phase is CO2, 25% MeOH (containing 0.2% iPrNH₂) hold 18 min, 15-50% MeOH (containing 0.2% iPrNH₂) hold 4.10 min.

Method 2:
In addition to the general procedure A: The chiral separation in SFC was carried out on a CHIRALCEL OD-H column (4.6×250 mm) at 030° C. with a flow rate of 3.0 ml/min. The mobile phase is CO2, 35% MeOH (containing 0.2% iPrNH₂) hold 15 min.

TABLE 6

Analytical SFC-MS Methods (Flow expressed in mL/min; column temperature (T) in ° C.; Pressure in bars).

| Method | Column | Mobile Phase | Flow | T | Pressure |
|---|---|---|---|---|---|
| 3 | Chiralcel OD-H 150 × 4.6 mm 5 µm Daicel | CO2/EtOH(0.3% IPrNH2) 70/30 | 3 | 35 | 100 |
| 4 | Chiralcel OD-H 150 × 4.6 mm 5 µm Daicel | CO2/EtOH(0.3% IPrNH2) 60/40 | 3 | 35 | 100 |
| 5 | Chiralpak AD-H 150 × 4.6 mm 5 µm Daicel | CO2/EtOH(0.3% IPrNH2) 80/20 | 3 | 35 | 100 |
| 6 | Chiralpak AD-H 150 × 4.6 mm 5 µm Daicel | CO2/iPrOH(0.3% IPrNH2) 80/20 | 3 | 35 | 100 |

TABLE 7

Analytical SFC data - $R_t$ means retention time (in minutes), [M + H]⁺ means the protonated mass of the compound, method refers to the method used for (SFC)MS analysis of enantiomerically pure compounds.

| Co. Nr. | $R_t$ | [M + H]⁺ | UV Area % | Method | Isomer Elution Order |
|---|---|---|---|---|---|
| 3 | 5.74 | 408 | 100 | 1 | A |
| 4 | 10.47 | 408 | 100 | 1 | B |
| 7 | 4.58 | 402 | 100 | 2 | A |
| 8 | 8.55 | 402 | 100 | 2 | B |
| 19 | 2.30 | 415 | 100 | 3 | A |
| 20 | 3.54 | 415 | 100 | 3 | B |
| 25 | 1.97 | 406. | 100 | 4 | A |
| 26 | 4.09 | 406 | 100 | 4 | B |
| 27 | 2.52 | 412 | 100 | 3 | A |
| 28 | 2.36 | 383 | 100 | 5 | B |
| 29 | 1.62 | 456 | 100 | 3 | A |
| 30 | 2.36 | 456 | 100 | 3 | B |
| 31 | 2.13 | 480 | 100 | 3 | A |
| 32 | 4.29 | 480 | 100 | 3 | B |
| 33 | 2.79 | 459 | 100 | 3 | A |
| 34 | 4.56 | 412 | 98.8 | 3 | B |
| 35 | 2.14 | 385 | 100 | 6 | A |
| 36 | 3.02 | 385 | 100 | 6 | B |
| 37 | 1.62 | 383 | 100 | 5 | A |
| 38 | 2.73 | 378 | 100 | 5 | A |
| 39 | 5.19 | 378 | 100 | 5 | B |
| 41 | 4.37 | 459 | 99.7 | 3 | B |

Isomer Elution Order: A means first eluting isomer; B means second eluting isomer.

NMR

For a number of compounds, ¹H NMR spectra were recorded on a Bruker Avance III with a 300 MHz Ultrashield magnet, on a Bruker DPX-400 spectrometer operating at 400 MHz, on a Bruker Avance I operating at 500 MHz, on a Bruker DPX-360 operating at 360 MHz, or on a Bruker Avance 600 spectrometer operating at 600 MHz, using CHLOROFORM-d (deuterated chloroform, CDCl₃) or DMSO-d₆ (deuterated DMSO, dimethyl-d6 sulfoxide) as solvent. Chemical shifts (δ) are reported in parts per million (ppm) relative to tetramethylsilane (TMS), which was used as internal standard.

TABLE 7

¹H NMR results

| Co. No. | ¹H NMR result |
|---|---|
| 1 | (600 MHz, DMSO-d₆) δ ppm 1.48 (t, J = 12.8 Hz, 1 H), 1.50 (s, 3 H), 1.99-2.05 (m, 1 H), 2.06-2.12 (m, 1 H), 2.25-2.33 (m, 1 H), 2.41 (d, J = 12.3 Hz, 1 H), 5.79 (br. s., 2 H), 7.44-7.51 (m, 2 H), 7.58-7.65 (m, 1 H), 7.70-7.75 (m, 1 H), 9.11 (s, 2 H), 9.18 (s, 1 H). |
| 2 | (400 MHz, CHLOROFORM-d) δ ppm 1.50 (t, J = 13.1 Hz, 1 H), 1.53-1.57 (m, 3 H), 2.11-2.32 (m, 2 H), 2.42 (ddd, J = 16.8, 5.8, 1.5 Hz, 1 H), 2.77 (br. s., 1 H), 7.43 (dt, J = 7.5, 1.5 Hz, 1 H), 7.49 (t, J = 7.7 Hz, 1 H), 7.55 (dt, J = 7.8, 1.5 Hz, 1 H), 7.72 (t, J = 1.6 Hz, 1 H), 8.96 (s, 2 H), 9.20 (s, 1 H). |

TABLE 7-continued

<sup>1</sup>H NMR results

| Co. No. | <sup>1</sup>H NMR result |
|---|---|
| 3 | (360 MHz, DMSO-$d_6$) δ ppm 1.41-1.50 (m, 1 H), 1.46 (s, 3 H), 2.01-2.14 (m, 2 H), 2.21 (br. d, J = 12.7 Hz, 1 H), 2.29 (d, J = 11.5 Hz, 1 H), 4.02 (s, 3 H), 5.79 (br. s., 2 H), 7.10 (br. d, J = 7.8 Hz, 1 H), 7.29 (t, J = 7.9 Hz, 1 H), 7.73 (t, J = 1.9 Hz, 1 H), 7.76 (br. d, J = 8.0 Hz, 1 H), 8.42 (d, J = 1.3 Hz, 1 H), 8.90 (d, J = 1.3 Hz, 1 H), 10.39 (br. s., 1 H). |
| 4 | (360 MHz, CHLOROFORM-d) δ ppm 1.49 (t, J = 13.3 Hz, 1 H), 1.53 (s, 3 H), 2.15-2.29 (m, 2 H), 2.41 (dd, J = 16.5, 5.7 Hz, 1 H), 2.64-2.84 (m, 1H), 3.30 (br. s., 2 H), 4.07 (s, 3 H), 7.24 (d, J = 7.7 Hz, 1 H), 7.36 (t, J = 7.9 Hz, 1 H), 7.71 (ddd, J = 8.0, 2.1, 1.00 Hz, 1 H), 7.78 (t, J = 1.9 Hz, 1 H), 8.15 (d, J = 1.3 Hz, 1 H), 9.03 (d, J = 1.3 Hz, 1 H), 9.54 (br. s., 1 H). |
| 9 | (360 MHz, DMSO-$d_6$) δ ppm 1.37-1.46 (m, 1 H), 1.50-1.56 (m, 3 H), 1.98-2.12 (m, 2 H), 2.31 (br. d, J = 11.0 Hz, 1 H), 2.44 (br. d, J = 12.8 Hz, 1 H), 4.02 (s, 3 H), 5.85 (br. s., 2H), 7.14 (dd, J = 12.0, 8.8 Hz, 1 H), 7.59 (dd, J = 7.6, 2.8 Hz, 1 H), 7.76 (ddd, J = 8.8, 4.2, 2.8 Hz, 1 H), 8.42 (d, J = 1.3 Hz, 1 H), 8.88 (d, J = 1.3 Hz, 1 H), 10.44 (br. s., 1 H). |
| 14 | (500 MHz, DMSO-$d_6$) δ ppm 1.49 (s, 3H), 2.64 (dd, J = 17.0, 2.2 Hz, 1H), 3.11-3.21 (m, 2H), 6.26 (br, 2H), 7.30 (dd, J = 11.7, 8.4 Hz, 1H), 7.73 (ddd, J = 8.4, 4.5, 2.5 Hz, 1H), 8.06 (dd, J = 7.3, 2.4 Hz, 1H), 9.01 (s, 2H), 9.18 (s, 1H). |
| 15 | (400 MHz, CHLOROFORM-d) δ ppm 1.60 (s, 3H), 2.87 (dd, J = 16.6, 2.6 Hz, 1H), 3.07-3.16 (m, 1H), 3.21-3.33 (m, 1H), 4.66 (br, 2H), 7.04 (dd, J = 11.2, 8.9 Hz, 1H), 7.75 (dd, J = 6.7, 2.8 Hz, 1H), 7.86 (dd, J = 8.4, 2.4 Hz, 1H), 8.05 (ddd, J = 8.8, 4.2, 3.0 Hz, 1H), 8.23 (dd, J = 8.4, 0.6 Hz, 1H), 8.54 (dd, J = 2.3, 0.5 Hz, 1H), 9.85 (br, 1H). |
| 16 | (500 MHz, DMSO-$d_6$) δ ppm 1.44 (s, 3 H), 2.50 (s, 3 H), 2.61 (dd, J = 16.9, 2.5 Hz, 1 H), 3.09 (dd, J = 16.8, 8.7 Hz, 1 H), 3.21-3.34 (m, 1 H), 6.11 (s, 2 H), 7.04 (dd, J = 11.4, 8.8 Hz, 1 H), 7.64 (ddd, J = 9.0, 4.3, 2.9 Hz, 1 H), 8.07 (dd, J = 6.9, 2.9 Hz, 1 H), 8.59 (s, 1 H), 10.02 (s, 1 H) |
| 17 | (500 MHz, DMSO-$d_6$) δ ppm 1.63 (br. s., 3 H), 2.80 (d, J = 16.8 Hz, 1 H), 3.22 (dd, J = 17.1, 9.0 Hz, 1 H), 3.50 (br. s., 1 H), 4.02 (s, 3 H), 7.14 (dd, J = 11.6, 9.0 Hz, 1 H), 7.33 (br. s., 2 H), 7.80 (dd, J = 7.2, 2.6 Hz, 1 H), 8.14 (dd, J = 7.2, 2.6 Hz, 1 H), 8.40 (d, J = 1.4 Hz, 1 H), 8.88 (d, J = 1.4 Hz, 1 H), 10.52 (br. s., 1 H) |
| 18 | (400 MHz, DMSO-$d_6$) δ ppm 1.45 (s, 3 H), 2.62 (dd, J = 16.9, 2.3 Hz, 1 H), 3.11 (dd, J = 16.8, 8.7 Hz, 1 H), 3.23-3.36 (m, 1 H), 6.16 (br. s, 2 H), 7.10 (dd, J = 11.3, 8.8 Hz, 1 H), 7.72 (ddd, J = 8.8, 4.4, 3.0 Hz, 1 H), 8.23 (dd, J = 6.9, 2.8 Hz, 1 H), 8.26 (dd, J = 8.1, 0.9 Hz, 1 H), 8.57 (dd, J = 8.2, 2.0 Hz, 1 H), 9.18 (dd, J = 2.1, 0.9 Hz, 1 H), 10.75 (br. s, 1 H) |
| 21 | 1.45 (s, 3 H), 2.62 (dd, J = 16.9, 3.0 Hz, 1 H), 3.06 (dd, J = 16.8, 8.7 Hz, 1 H), 3.18-3.32 (m, 1 H), 3.86 (s, 3 H), 6.07 (br. s, 2 H), 6.72 (d, J = 7.9, 5.1 Hz, 1 H), 6.96 (dd, J = 11.6, 8.8 Hz, 1 H), 7.17 (dd, J = 7.9, 1.4 Hz, 1 H), 7.68 (dd, J = 4.9, 1.4 Hz, 1 H), 7.82 (dd, J = 6.9, 2.8 Hz, 1 H), 7.83-7.89 (m, 1 H), 8.01 (br. s, 1 H). |
| 22 | <sup>1</sup>H NMR (400 MHz, CDCl$_3$) δ ppm 1.61 (d, J = 0.9 Hz, 3 H), 2.81 (dd, J = 16.6, 2.6 Hz, 1 H), 3.10 (dd, J = 16.6, 8.6 Hz, 1 H), 3.20-3.33 (m, 1 H), 4.29 (br. s., 2 H), 6.76 (dd, J = 7.6, 5.1 Hz, 1 H), 7.04 (br. s., 1 H), 7.02 (dd, J = 11.3, 8.8 Hz, 1 H), 7.61 (dd, J = 6.5, 2.8 Hz, 1 H), 7.76 (dd, J = 7.6, 2.1 Hz, 1 H), 7.83 (ddd, J = 8.8, 4.3, 2.9 Hz, 1 H), 8.36 (dd, J = 4.9, 2.1 Hz, 1 H) |
| 23 | (500 MHz, DMSO-$d_6$) δ ppm 1.45 (s, 3 H), 2.62 (dd, J = 16.8, 2.4 Hz, 1 H), 3.09 (dd, J = 17.2, 9.1 Hz, 1 H), 3.22-3.35 (m, 1 H), 3.31 (s, 3 H), 3.69-3.73 (m, 2 H), 4.49-4.54 (m, 2 H), 6.14 (br. s, 2 H), 7.07 (dd, J = 11.4, 8.7 Hz, 1 H), 7.68 (ddd, J = 8.6, 4.2, 2.9 Hz, 1 H), 8.16 (dd, J = 6.9, 2.8 Hz, 1 H), 8.40 (d, J = 1.2 Hz, 1 H), 8.84 (d, J = 1.4 Hz, 1 H), 10.41 (br. s, 1 H) |
| 24 | (400 MHz, DMSO-$d_6$) δ ppm 1.45 (s, 3 H), 2.62 (dd, J = 16.9, 2.3 Hz, 1 H), 3.10 (dd, J = 16.8, 8.7 Hz, 1 H), 3.22-3.36 (m, 1 H), 5.16 (q, J = 8.8 Hz, 2 H), 6.14 (br. s, 2 H), 7.08 (dd, J = 11.6, 8.8 Hz, 1 H), 7.69 (ddd, J = 9.0, 4.4, 2.8 Hz, 1 H), 8.20 (dd, J = 7.1, 2.7 Hz, 1 H), 8.60 (d, J = 1.4 Hz, 1 H), 8.90 (d, J = 1.4 Hz, 1 H), 10.52 (br. s, 1 H) |
| 30 | (500 MHz, DMSO-$d_6$) δ ppm 1.46 (s, 3 H), 2.63 (dd, J = 16.8, 2.3 Hz, 1 H), 3.10 (dd, J = 16.8, 8.7 Hz, 1 H), 3.31 (s, 3 H), 3.24-3.37 (m, 1 H), 3.69-3.75 (m, 2 H), 4.50-4.56 (m, 2 H), 6.23 (br. s., 2 H), 7.08 (dd, J = 11.6, 8.7 Hz, 1 H), 7.66-7.72 (m, 1 H), 8.19 (dd, J = 7.1, 2.7 Hz, 1 H), 8.42 (d, J = 1.4 Hz, 1 H), 8.85 (d, J = 1.2 Hz, 1 H), 10.42 (br. s, 1 H) |
| 33 | (500 MHz, DMSO-$d_6$) δ ppm 1.45 (s, 3H), 2.62 (dd, J = 16.8, 2.3 Hz, 1H), 3.10 (br dd, J = 16.9, 8.5 Hz, 1H), 3.19-3.31 (m, 1H), 6.15 (br s, 2H), 7.08 (dd, J = 11.4, 8.8 Hz, 1H), 7.67-7.75 (m, 1H), 8.06 (dd, J = 8.1 Hz, 1H), 8.18 (dd, J = 6.9, 2.6 Hz, 1H), 8.32 (dd, J = 8.4, 2.3 Hz, 1H), 8.84 (d, J = 1.7 Hz, 1H), 10.56 (s, 1H) |
| 38 | <sup>1</sup>H NMR (400 MHz, DMSO-$d_6$) δ = 9.16 (s, 1H), 8.31 (dd, J = 1.8, 4.9 Hz, 1H), 8.05 (dd, J = 2.1, 7.6 Hz, 1H), 7.75 (dd, J = 3.0, 6.9 Hz, 1H), 7.49 (td, J = 4.3, 7.3 Hz, 1H), 7.01 (dd, J = 8.8, 11.3 Hz, 1H), 6.87 (dd, J = 4.9, 7.6 Hz, 1H), 6.09 (s, 2H), 3.33-3.21 (m, 1H), 3.10 (dd, J = 8.7, 16.8 Hz, 1H), 2.60 (br dd, J = 2.5, 16.9 Hz, 1H), 1.44 (s, 3H). |
| 40 | <sup>1</sup>H NMR (500 MHz, DMSO-$d_6$) δ = 10.56 (s, 1H), 8.84 (d, J = 1.7 Hz, 1H), 8.32 (dd, J = 2.3, 8.4 Hz, 1H), 8.18 (dd, J = 2.6, 6.9 Hz, 1H), 8.06 (d, J = 8.1 Hz, 1H), 7.75-7.67 (m, 1H), 7.08 (dd, J = 8.8, 11.4 Hz, 1H), 6.15 (br s, 2H), 3.31-3.19 (m, 1H), 3.10 (br dd, J = 8.5, 16.9 Hz, 1H), 2.62 (dd, J = 2.3, 16.8 Hz, 1H), 1.45 (s, 3H) |

D. Pharmacological Examples

The compounds provided in the present invention are inhibitors of the beta-site APP-cleaving enzyme 1 (BACE1). Inhibition of BACE1, an aspartic protease, is believed to be relevant for treatment of Alzheimer's Disease (AD). The production and accumulation of beta-amyloid peptides (Abeta) from the beta-amyloid precursor protein (APP) is believed to play a key role in the onset and progression of AD. Abeta is produced from the amyloid precursor protein (APP) by sequential cleavage at the N- and C-termini of the Abeta domain by beta-secretase and gamma-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular αLisa assay in SKNBE2 cells described below and which are suitable for the identification of such compounds, and more particularly the compounds according to Formula (I), are shown in Table 8 and Table 9.

BACE1 Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) beta-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis.

Method 1

Briefly in a 384-well format recombinant BACE1 protein in a final concentration of 1 µg/ml is incubated for 120 minutes at room temperature with 10 µm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU (Relative Fluorescence Units), as difference between T120 and T0.

A best-fit curve is fitted by a minimum sum of squares method to the plot of % Controlmin versus compound concentration. From this an $IC_{50}$ value (inhibitory concentration causing 50% inhibition of activity) can be obtained.

$LC$ = Median of the low control values

= Low control: Reaction without enzyme $HC$ = Median of the High control values

= High Control: Reaction with enzyme

%Effect = $100 - [(sample - LC)/(HC - LC) * 100]$

%Control = $(sample/HC) * 100$

%Controlmin = $(sample - LC)/(HC - LC) * 100$

Method 2

Briefly in a 384-well format recombinant BACE1 protein in a final concentration of 0.04 µg/ml is incubated for 450 minutes at room temperature with 20 µM substrate in incubation buffer (50 mM Citrate buffer pH 5.0, 0.05% PEG) in the presence of compound or DMSO. Next the amount of proteolysis is directly measured by fluorescence measurement (excitation at 320 nm and emission at 405 nm) at different incubation times (0, 30, 60, 90, 120 and 450 min). For every experiment a time curve (every 30 min between 0 min and 120 min) is used to determine the time where we find the lowest basal signal of the high control. The signal at this time (Tx) is used to subtract from the signal at 450 min. Results are expressed in RFU, as difference between T450 and Tx.

A best-fit curve is fitted by a minimum sum of squares method to the plot of % Controlmin versus compound concentration. From this an $IC_{50}$ value (inhibitory concentration causing 50% inhibition of activity) can be obtained.

$LC$ = Median of the low control values

= Low control: Reaction without enzyme $HC$ = Median of the High control values

= High Control: Reaction with enzyme

%Effect = $100 - [(sample - LC)/(HC - LC) * 100]$

%Control = $(sample/HC) * 100$

%Controlmin = $(sample - LC)/(HC - LC) * 100$

The following exemplified compounds were tested essentially as described above and exhibited the following the activity:

TABLE 8

| Co. Nr. | Biochemical FRET based assay - Method 1 $pIC_{50}$ | Biochemical FRET based assay - Method 2 $pIC_{50}$ |
| --- | --- | --- |
| 1 | 5.83 | 5.99 |
| 2 | 4.74 | <5 |
| 3 | 7.5 | 7.6 |
| 4 | <4.52 | <5 |
| 5 | 7.58 | 7.74 |
| 6 | 5.31 | 5.79 |
| 7 | 7.49 | 7.69 |
| 8 | 5.01 | 5.17 |
| 9 | 7.41 | 8.12 |
| 10 | 7.44 | 8.44 |
| 11 | 7.51 | 8.58 |
| 12 | 7.29 | 7.81 |
| 13 | 7.41 | 8.21 |
| 14 | n.t. | <5 |
| 15 | n.t. | 6.31 |
| 16 | n.t. | 5.94 |
| 17 | n.t. | 6.06 |
| 18 | n.t. | 6.42 |
| 19 | n.t. | 6.52 |
| 20 | n.t. | <5 |
| 21 | n.t. | 5.62 |
| 22 | n.t. | 5.43 |
| 23 | n.t. | 6.11 |
| 24 | n.t. | 6.10 |
| 25 | n.t. | 6.74 |
| 26 | n.t. | <5 |
| 27 | n.t. | 6.41 |
| 28 | n.t. | 5.92 |
| 29 | n.t. | 6.35 |
| 30 | n.t. | <5 |

TABLE 8-continued

| Co. Nr. | Biochemical FRET based assay - Method 1 pIC$_{50}$ | Biochemical FRET based assay- Method 2 pIC$_{50}$ |
|---|---|---|
| 31 | n.t. | 6.34 |
| 32 | n.t. | <5 |
| 33 | n.t. | 6.64 |
| 34 | n.t. | <5 |
| 35 | n.t. | <5 |
| 36 | n.t. | 5.99 |
| 37 | n.t. | <5 |
| 38 | n.t. | <5 |
| 39 | n.t. | 5.53 |
| 40 | n.t. | 6.49 |
| 41 | n.t. | <5 | n.t. means not tested

Cellular αLisa Assay in SKNBE2 Cells

In two αLisa assays the levels of Abeta total and Abeta 1-42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Abeta 1-42 and Abeta total are taken. Abeta total and Abeta 1-42 are measured by sandwich αLisa. αLisa is a sandwich assay using biotinylated antibody AbN/25 attached to streptavidin coated beads and antibody Ab4G8 or cAb42/26 conjugated acceptor beads for the detection of Abeta total and Abeta 1-42 respectively. In the presence of Abeta total or Abeta 1-42, the beads come into close proximity. The excitation of the donor beads provokes the release of singlet oxygen molecules that trigger a cascade of energy transfer in the acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an IC$_{50}$ value (inhibitory concentration causing 50% inhibition of activity) can be obtained.

LC = Median of the low control values
= Low control: cells preincubated without compound, without biotinylated Ab in the αLisa HC = Median of the High control values
= High Control: cells preincubated without compound %Effect = 100 − [(sample − LC)/(HC − LC) * 100]

%Control = (sample/HC) * 100

%Controlmin = (sample − LC)/(HC − LC) * 100

The following exemplified compounds were tested essentially as described above and exhibited the following activity:

TABLE 9

| Co. Nr. | Cellular αLisa assay in SKNBE2 cells Abeta 42 pIC$_{50}$ | Cellular αLisa assay in SKNBE2 cells Abeta total pIC$_{50}$ |
|---|---|---|
| 1 | 6.53 | 6.58 |
| 2 | 5.37 | 5.4 |

TABLE 9-continued

| Co. Nr. | Cellular αLisa assay in SKNBE2 cells Abeta 42 pIC$_{50}$ | Cellular αLisa assay in SKNBE2 cells Abeta total pIC$_{50}$ |
|---|---|---|
| 3 | 8.02 | 8.06 |
| 4 | 5.63 | 5.71 |
| 5 | 7.62 | 7.68 |
| 6 | 5.7 | 5.73 |
| 7 | 7.62 | 7.62 |
| 8 | 5.64 | 5.6 |
| 9 | 8.28 | 8.23 |
| 10 | 8.37 | 8.42 |
| 11 | 8.63 | 8.7 |
| 12 | 8.12 | 8.11 |
| 13 | 7.65 | 7.62 |
| 14 | 5.05 | 5.08 |
| 15 | 7 | 6.89 |
| 16 | 6.60 | 6.62 |
| 17 | 6.77 | 6.75 |
| 18 | 7.17 | 7.19 |
| 19 | 7.21 | 7.09 |
| 20 | 5.05 | 5.08 |
| 21 | 6.41 | n.t. |
| 22 | 6.11 | n.t. |
| 23 | 6.46 | n.t. |
| 24 | 6.38 | n.t. |
| 25 | 7.22 | n.t. |
| 26 | <5.05 | n.t. |
| 27 | 7.00 | n.t. |
| 28 | 6.46 | n.t. |
| 29 | 6.82 | n.t. |
| 30 | <5.05 | n.t. |
| 31 | 6.59 | n.t. |
| 32 | <5.05 | n.t. |
| 33 | 7.44 | n.t. | n.t. means not tested

BACE2 Biochemical FRET Based Assay

This assay is a Fluorescence Resonance Energy Transfer Assay (FRET) based assay. The substrate for this assay contains the 'Swedish' Lys-Met/Asn-Leu mutation of the amyloid precursor protein (APP) beta-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by the beta-secretase, the fluorophore Mca is separated from the quenching group Dnp, restoring the full fluorescence yield of the donor. The increase in fluorescence is linearly related to the rate of proteolysis.

Briefly in a 384-well format recombinant BACE2 protein in a final concentration of 0.4 µg/nil is incubated for 450 minutes at room temperature with 10 µM substrate in incubation buffer (50 mM Citrate buffer pH 5.0, 0.05% PEG, no DMSO) in the absence or presence of compound. Next the amount of proteolysis is directly measured by fluorescence measurement at T=0 and T=450 (excitation at 320 nm and emission at 405 nm). Results are expressed in RFU (Relative Fluorescence Units), as difference between T450 and T0.

A best-fit curve is fitted by a minimum sum of squares method to the plot of % Controlmin versus compound concentration. From this an IC$_{50}$ value (inhibitory concentration causing 50% inhibition of activity) can be obtained.

LC = Median of the low control values
   = Low control: Reaction without enzyme

HC = Median of the High control values
   = High Control: Reaction with enzyme

%Effect = 100 − [(sample − LC)/(HC − LC) ∗ 100]

%Control = (sample/HC) ∗ 100

%Controlmin = (sample − LC)/(HC − LC) ∗ 100

The following exemplified compounds were tested essentially as described above and exhibited the following the activity:

TABLE 10

| Co. Nr. | Biochemical FRET based assay pIC$_{50}$ |
|---|---|
| 1 | 4. |
| 2 | <5 |
| 3 | 6.47 |
| 4 | <5 |
| 5 | 7.68 |
| 6 | 5.94 |
| 7 | 6.88 |
| 8 | <5 |
| 9 | 7.17 |
| 10 | 7.59 |
| 11 | 8.39 |
| 12 | 7.97 |
| 13 | 8.51 |
| 14 | <5 |
| 15 | 6.04 |
| 16 | 6.27 |
| 17 | <5 |
| 18 | 5.66 |
| 19 | 6.16 |
| 20 | <5 |
| 21 | 6.03 |
| 22 | .5 |
| 23 | <5 |
| 24 | <5 |
| 25 | 5.97 |
| 26 | <5 |
| 27 | 5.23 |
| 28 | 6.21 |
| 29 | <4.7 |
| 30 | <4.7 |
| 31 | <4.7 |
| 32 | <4.7 |
| 33 | 6.29 | n.t. means not tested

The invention claimed is:
1. A compound of Formula (I)

or a tautomer or a stereoisomeric form thereof, wherein
n is 0 or 1;
$R^1$ is hydrogen, $C_{1-3}$alkyl, cyclopropyl, mono- and polyhalo-$C_{1-3}$alkyl;
$R^2$ is hydrogen or fluoro;
L is a bond or —NHCO—;
Ar is homoaryl or heteroaryl;
   wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy; and
   wherein heteroaryl is selected from the group consisting of pyridyl, pyrimidyl, pyrazyl, pyridazyl, furanyl, thienyl, pyrrolyl, pyrazolyl, imidazolyl, triazolyl, tetrazolyl, thiazolyl, isothiazolyl, thiadiazolyl, oxazolyl, isoxazolyl, and oxadiazolyl, each optionally substituted with one, two or three substituents selected from the group consisting of halo, cyano, $C_{1-3}$alkyl, $C_{2-3}$alkynyl, $C_{1-3}$alkyloxy, mono- and polyhalo-$C_{1-3}$alkyl, mono- and polyhalo-$C_{1-3}$alkyloxy, and $C_{1-3}$alkyloxy$C_{1-3}$alkyloxy;
or a pharmaceutically acceptable acid addition salt thereof.

2. The compound of claim 1 wherein $R^1$ is methyl.

3. The compound of claim 1 wherein $R^2$ is hydrogen.

4. The compound of claim 1 wherein L is NH—C(=O)—.

5. The compound of claim 1 wherein Ar is pyridinyl or pyrazinyl substituted with one or two halo atoms or $C_{1-3}$alkyloxy.

6. The compound of claim 1 wherein $R^1$ is methyl, $R^2$ is hydrogen, L is NH—C(=O)— and Ar is pyridinyl or pyrazinyl substituted with one or two halo atoms or $C_{1-3}$alkyloxy.

7. The compound of claim 1 wherein $R^1$ is methyl, $R^2$ is hydrogen, L is —NH—C(=O)— and Ar is 5-methoxy-pyrazin-2-yl, 5-bromo-pyridin-2-yl, 5-chloro-3-fluoro-pyridin-2-yl or 5-cyano-pyridin-2-yl.

8. The compound of claim 1 wherein $R^2$ is fluoro.

9. The compound of claim 1 wherein n is 1.

10. The compound of claim 1 wherein $R^1$ is methyl, $R^2$ is fluoro, n is 1, L is —NH—C(=O)— and Ar is 5-methoxy-pyrazin-2-yl, 5-chloro-pyridin-2-yl, 5-fluoro-pyridin-2-yl, 5-cyano-pyridin-2-yl, 5-chloro-3-fluoro-pyridin-2-yl or 1-difluoromethyl-pyrazol-3-yl.

11. A pharmaceutical composition comprising a therapeutically effective amount of a compound according to claim 1 and a pharmaceutically acceptable carrier.

12. A process for preparing a pharmaceutical composition comprising mixing a pharmaceutically acceptable carrier with a therapeutically effective amount of a compound according to claim 1.

13. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease, dementia associated with beta-amyloid, age-related macular degeneration, type 2 diabetes and metabolic disorders comprising administering to a subject in need thereof, a therapeutically effective amount of a compound according to claim 1.

14. A method for modulating beta-site amyloid cleaving enzyme activity, comprising administering to a subject in need thereof, a therapeutically effective amount of a compound according to claim 1.

15. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease, dementia associated with beta-amyloid, age-related macular degeneration, type 2 diabetes and metabolic disorders comprising administering to a subject in need thereof, a therapeutically effective amount of a pharmaceutical composition according to claim 11.

16. A method for modulating beta-site amyloid cleaving enzyme activity, comprising administering to a subject in need thereof, a therapeutically effective amount of a pharmaceutical composition according to claim 11.

* * * * *